United States Patent [19]

Shikani et al.

[11] Patent Number: 5,762,638

[45] Date of Patent: Jun. 9, 1998

[54] ANTI-INFECTIVE AND ANTI-INFLAMMATORY RELEASING SYSTEMS FOR MEDICAL DEVICES

[76] Inventors: Alain H. Shikani, 11 Johnson Mill Rd., Ruxton, Md. 21204; Abraham J. Domb, 16 Migdal Eder Street, Efrat, Israel

[21] Appl. No.: 601,251

[22] Filed: Feb. 14, 1996

Related U.S. Application Data

[63] Continuation-in-part of Ser. No. 316,067, Sep. 30, 1994, Pat. No. 5,512,055, which is a continuation of Ser. No. 998,773, Dec. 22, 1992, abandoned, which is a continuation of Ser. No. 661,699, Feb. 27, 1991, abandoned.

[51] Int. Cl.$^6$ .......................... A61M 5/32; A61M 25/00
[52] U.S. Cl. .......................... 604/265; 604/264; 604/890.1; 604/891.1; 128/207.14
[58] Field of Search .......................... 128/207.14, 207.15; 604/890.1, 891.1, 892.1, 264, 265, 280; 623/1, 11, 12

[56] References Cited

U.S. PATENT DOCUMENTS

| | | | |
|---|---|---|---|
| 3,235,446 | 2/1966 | Shelanski et al. | 167/17 |
| 3,566,874 | 3/1971 | Shepherd et al. | 128/349 |
| 3,598,127 | 8/1971 | Wepsic | 128/349 |
| 3,898,326 | 8/1975 | Cantor et al. | 424/80 |
| 4,010,259 | 3/1977 | Johansson | 424/150 |
| 4,017,407 | 4/1977 | Cantor et al. | 252/106 |
| 4,054,139 | 10/1977 | Crossley | 128/260 |
| 4,186,745 | 2/1980 | Lewis et al. | 128/260 |
| 4,381,380 | 4/1983 | LaVeen et al. | 525/452 |
| 4,392,848 | 7/1983 | Lucas et al. | 604/53 |
| 4,479,795 | 10/1984 | Mustacich et al. | 604/53 |
| 4,603,152 | 7/1986 | Laurin et al. | 604/265 |
| 4,642,104 | 2/1987 | Sakamoto et al. | 604/264 |
| 4,677,143 | 6/1987 | Laurin et al. | 424/618 |
| 4,879,135 | 11/1989 | Greco et al. | 427/2 |
| 4,917,686 | 4/1990 | Bayston et al. | 604/265 |
| 4,994,047 | 2/1991 | Walker et al. | 604/264 |
| 5,019,096 | 5/1991 | Fox, Jr. et al. | 623/1 |
| 5,102,401 | 4/1992 | Lambert et al. | 604/264 |
| 5,165,952 | 11/1992 | Solomon et al. | 427/2 |
| 5,344,411 | 9/1994 | Domb et al. | 604/265 |
| 5,437,656 | 8/1995 | Shikani et al. | 604/265 |
| 5,512,055 | 4/1996 | Domb et al. | 604/265 |

OTHER PUBLICATIONS

The Merck Index: An Encyclopedia of Chemicals, Drugs and Biologicals, tenth edition, p. 425, 1983.

*Primary Examiner*—Mark Bockelman
*Assistant Examiner*—Jennifer R. Sadula
*Attorney, Agent, or Firm*—Leonard Bloom

[57] ABSTRACT

Medical devices for implantation into the body are coated with anti-infective and or anti-inflammatory agents. The medical devices can be, for example, endotracheal/tracheostomy tubes and catheters. The devices have a polymer coating containing an anti-infective agent and/or an anti-inflammatory agent. The preferred anti-infective agent is iodine and the preferred anti-inflammatory agent is steroidal.

1 Claim, 20 Drawing Sheets

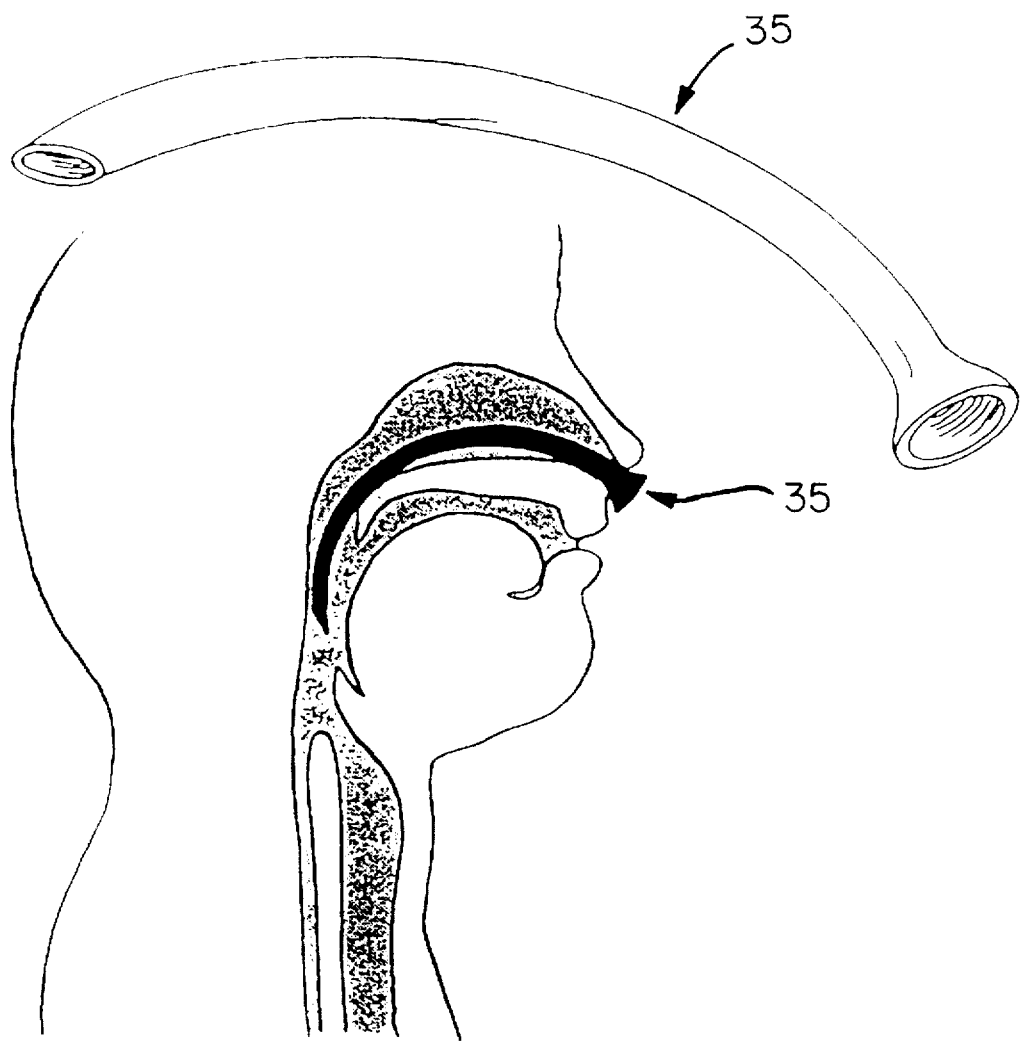

ANTI-INFECTIVE AND ANTI-INFLAMMATORY RELEASING SYSTEMS FOR MEDICAL DEVICES

CROSS-REFERENCE TO RELATED APPLICATION

The present application is a continuation-in-part of U.S. patent application, Ser. No. 08/316,067 filed Sep. 30, 1994 now U.SD. Pat. No. 5,512,055, which was a continuation of Ser. No. 07/998,773 filed Dec. 22, 1992 (now abandoned) which was a continuation of Ser. No. 07/661,699 filed Feb. 27, 1991 (now abandoned), the disclosures of which are hereby incorporated herein in their entirety.

BACKGROUND OF THE INVENTION

The present invention relates to invasive medical devices and to the delayed/sustained release of pharmaceutical compositions from a polymer that has been coated or incorporated into the devices. The purpose of the coating or delivery system on these devices is to reduce, control or even prevent the inflammation and infection that may occur with prolonged inserted use.

A longstanding problem in the area of medical devices, such as tubes and catheters directly contacting the mucosa and other tissue of the body, for prolonged periods of time, is the reaction by the body to these devices. This reaction is seen in the use of various tubes, such as, endotracheal tubes, tracheal tubes, ear ventilation (PE) tubes, gastrostomy tubes, foley catheters, intravenous catheters and the like. The reaction often consists of an inflammation and/or infection that frequently progresses into a pathological state.

Tracheotomy tubes are a well known, and well used, surgical devices. The tube is generally inserted through an incision made in the trachea and once in place is used to supply air, as well as a route for pulmonary cleaning. Prolonged intubation using tracheotomy tubes may cause tracheal stenosis. Prolonged intubation using endotracheal tubes may cause subglottic stenosis. Acquired subglottic stenosis, consequent to prolonged intubation, is a much dreaded and morbid condition. The endotracheal tube may cause pressure necrosis at the point of interface with tissue, leading to mucosal edema and ulceration. As ulceration deepens, there is an interruption of normal ciliary flow with mucociliary stasis leading to secondary infection and perichondritis.

The management of the problems set forth above is both controversial and frustrating, as evidenced by the wide spectrum of remedial therapeutic procedures advocated. The fact is that the advocated procedures give far from ideal results. Of the non-invasive therapeutic procedures available, systemic administration of corticosteroids, alone or with systemically administered antibiotics has been advocated. Corticosteroids are known to have an anti-inflammatory effect on the exudative and destructive phases of injury, as well as during the period of healing. The drawback to systemic steroid treatment is that it results in a generalized immunosuppression and a decrease in healing, as well as other undesirable side effects. Recently, inhaled aerolized corticosteroids have been shown to be quite beneficial in reducing the subglottic injury in animals.

Antimicrobial therapy has been advocated to control localized subglottic bacterial infection. Experimental studies in dogs has shown that proper timing (early treatment) and adequate duration of therapy after injury are of great importance in reducing the activity and sequelae of subglottic injury and subsequent sclerosing chondritis. (Reported by Croft, C., et al, *Laryngoscope* 89: 482–489 (1979).)

As a result of the prolonged insertion of the endotracheal or tracheotomy tube, granulation tissue may occur, not only perpetuating local infection but also at times blocking the airway and necessitating emergency surgical intervention to remove the granulation tissue. Experimental studies, in animals, have shown that the therapeutic key in this type of intubation is to achieve a high local concentration of antibiotics and to maintain the antibiotic treatment throughout the period of intubation. (Kryzer, T. C., (1990).) Systemic antibiotic treatment, until now, has not been the standard of clinical care because of high cost and the potential for side effects resulting from prolonged systemic treatment. It is to be noted that some patients need to remain intubated for weeks and hence need to keep this tube inserted for this long duration.

Another problem attendant to tube insertion involves ear ventilation (PE) tubes. Millions of PE tubes are inserted every year in the United States alone. Of all PE tube insertions, 20% result in chronic otorrhea and require systemic antibiotic treatment. Those patients who fail to respond to the systemic antibiotics, sometimes respond to local installation of antibiotics and corticosteroids, introduced into the ear canal. A certain number of patients will need removal of the tube, as reported by Bluestone and Stool, *Pediatric Otolaryngology*, pp. 321–486, 2nd edition (Saunders Publishing Co., Philadelphia 1990).

Infection and inflammation is perhaps most commonly encountered at the point where the catheter is inserted through the skin (which normally forms a natural barrier against infectants), as well as along the catheter's length. If the catheter has been inserted in body cavities, such as the bladder, ear or aero-digestive tract, infection and inflammation of these cavities may occur with formation of granulation tissue and blockage of these cavities. However, and more seriously, bacteria/fungi can colonize and migrate into the patient's body resulting in bacteremia/fungemia.

Further, if the catheter is positioned within the patient's body for a prolonged period of time, tissue growth (for example, granulation or fibrosis) may develop about the catheter, as a natural consequence of the body's natural defense mechanisms against the presence of the contaminant. Such tissue growth can form a glycocallix to which bacteria may adhere, multiply and then spread along the catheter into the body.

To compound the above-mentioned problems of infection, inflammation and tissue growth, often the only method of treatment is by changing the catheter and the administration of systemic antibiotics, etc. Unfortunately, such systemic treatment can be costly; and can result in change of bacterial flora and the emergence of resistance.

All-in-all, as can be readily understood, the above-mentioned problems of infection and inflammation represent grave problems of longstanding duration. These problems have curtailed the use of catheters, to the extent that standard catheters can be utilized only for several days at a time before they must be removed and a new one inserted. Such a situation creates a further problem in that the insertion and removal of the catheter (especially where central venous catheters are involved) can be a dangerous task.

The prior art has proposed fighting bacterial infection by incorporating and/or binding antibiotics and antimicrobial agents into various medical devices (such as catheters, bandages, implants, ocular inserts and intrauterine devices) which are inserted into a patient's body. Once inserted, antibiotic/anti-microbial agents are released or leeched therefrom for preventing infection. Examples of such devices are the catheters disclosed in U.S. Pat. No. 3,598,127 issued to Wepsic (a urinary tract catheter of nonpermeable rubber in which antibiotics,such as neomycin is infused); 4,186,745 (wherein antibacterial substances are infused into microporous polyethylene, polypropylene or polyfluorocarbon polymers); 4,054,139 issued to Crossley (wherein oligodynamic agents, such as metallic silver and other heavy metals are incorporated onto catheter surfaces); and 3,566,874 issued to Shepard (wherein antibiotics and germicides, such as penicillin and cetylpyridinium chloride are infused into a hydrophilic polymer for coating medical appliances). Other examples are disclosed in U.S. Pat. Nos. 4,603,152 issued to Lavrin; 4,642,104 issued to Sakamoto et al; 4,650,488 issued to Bays et al; 4,879,135 issued to Greco et al; 5,013,306 issued to Solomon et al; 5,028,597 issued to Kodama et al; 5,019,096 issued to Fox, Jr. et al; and 5,019,601 issued to Allen.

Efforts to incorporate antibiotic releasing coatings into catheters have been made. U.S. Pat. No. 4,950,256 to Luthoer and Shanbrom discloses an intravascular catheter having a polymeric coating incorporating an antibiotic. The antibiotic prevents bacterial growth on the catheter when inserted into a blood vessel of the patient. However, none of the prior art has addressed the more difficult problem of infection, inflammation and the growth of tissue around the catheter or tracheotomy tube.

While being generally useful, in varying degrees, for their intended purposes of fighting infection on a localized level, each of the prior art approaches suffers from one or more of the following disadvantages: (1) they merely involve mixtures of components and the antibacterial agent is neither chemically combined to the plastic nor slowly released; and (2) disclosures involving bioerodible coatings present the undesirable side effect of also releasing the bioerodible coating into the patient's body with all of the attendant problems that bioerosion presents.

Commonly-utilized and well-accepted for inhibiting infection is the use of iodine. Iodine is a broad spectrum antimicrobial agent that has bactericidal, fungicidal and viricidal properties. When iodine reacts with biological solutions, free iodine, which provides the germicidal effect, is released. While generally inhibiting infective germs over the short term, the biocidal effectiveness of iodine is dependent on, inter alia, how long the contaminant is exposed to it. This is particularly important in the case of HIV and HBV where the iodine is effective only after it remains in contact with the virus for a relatively long period of time (more than 10 minutes). Topically applied iodine released all at once does not provide adequate sustained protection. Further, such topical application is of little to no use in inhibiting internal infection either in the short term or in the long term.

To increase the effectiveness of iodine, it is normally incorporated into solutions, soaps, creams, pastes, etc., in the form of an iodophor. Such iodophors, in effect, provide a reservoir of iodine from which small amounts of free iodine in aqueous solution are released over a period of time. These iodophors are then topically applied to that area of a patient's body which is desired to be treated. Perhaps the best known of these iodophors is povidone-iodine, a compound of polyvinylpyrrolidone with iodine. An example of such an application can be found by reference to U.S. Pat. No. 4,010,259 issued to Johansson.

It has also been disclosed in U.S. Pat. No. 4,381,380 issued to Le Veen et al, to provide cross-linked thermoplastic polyurethane articles, such as catheters, into which iodine has been complexed for antibacterial use. While being useful for their purpose, such cross-linked thermoplastics cannot be utilized for coatings.

As is well-known, polymers, such as polyurethanes, may be either essentially cross-linked or essentially uncross-linked. The uncross-linked polymers are suitable for the production of coatings, but are not of a tensile strength which is acceptable to fashion appliances, such as catheters, which require more exacting physical properties. The cross-linked polymers are suitable for the production of appliances, but are not suitable for the production of coatings, such as the ones noted herein. Further, cross-linked polymers possess a stearic hinderance that renders inaccessible many, and sometimes all, of the linkages which complex with the iodine.

It would be extremely advantageous to provide a catheter, endotracheal tube or a tracheotomy tube which has a thermoset uncross-linked polymer coating that has iodine either complexed therein for quick and relative immediate release of the iodine and/or matrixed therein for sustained release of the iodine.

Thus, it can be seen that there remains a need for catheters, endotracheal tubes and tracheotomy tubes that are solvent coatable with a polymeric dispersion or solution that have iodine complexed and/or matrixed therein, so as to provide for immediate and/or sustained release of the iodine therefrom for inhibiting infection, that is commonly associated with the use of such catheters.

None of the prior art has coated a tube with a polymer coating which contains both an anti-infective agent and an anti-inflammatory agent in a programmable release form and which remain active for a long period of time.

In view of the difficulty and expense of systemically maintaining effectively high concentrations of drugs at the intubation site, the inventors have proposed the coating of the endotracheal tube or tracheostomy tube with a polymer that will release high, controlled concentrations of anti-inflammatory drugs (e.g. corticosteroids) and antimicrobial drugs. The coated endotracheal or tracheostomy tubes provide site-specific controlled and sustained release of anti-inflammatory (e.g. corticosteroid) and a antimicrobial agent, locally around the tube, in order to reduce, control and prevent inflammation, infection and granulation of tissue that occur with prolonged intubation. The proposed coating is expected to result in longer tolerance of the tube and lower incidence of complications from intubation, such as, subglottic stenosis and granulation tissue formation.

It is to be noted that another significant problem encountered is that contaminated catheters and medical devices represent a potential hazard to the general public as well as to health care providers and to workers engaged in disposal of medically contaminated waste. The presence of HIV and other infectious germs on catheters and medical waste is a potential source of infection to anyone contacting these materials. Procedures for proper disposal have been instituted but the problem has not been eliminated. A need exists for a means to inhibit the infective germs on catheters and contaminated waste to protect the health of all persons who may contact these products subsequent to contamination by diseased patients.

BRIEF SUMMARY OF THE INVENTION

It is an object of the present invention to provide medical devices which are anti-microbial and anti-inflammatory and thereby remedy the problems noted above.

It is a further object of the present invention to provide medical devices providing prolonged, low-dose, localized release of anti-microbial and/or anti-inflammatory agents.

It is a still further object to provide medical devices for insertion or implantation into tissue which will resist infection, inhibit inflammation and inhibit the growth of tissue around and onto the device.

It is an important object of this invention to provide medical devices for insertion or implantation into the body which will retain anti-infectivity during insertion or implantation, as well as after the device is removed from the body.

The invention herein disclosed is directed to medical devices for implantation into the body. Such devices encompass tubes, catheters and sponges having a polymer coating. The polymer coating contains therein effective amounts of an anti-infective agent and an anti-inflammatory agent. These agents will be capable of being released over a long period of time, once the coated medical device is inserted into the body and comes in contact with body fluids.

The preferred coated medical device contemplated by the inventors is a tube and, more specifically, a tracheal or endotracheal tube.

The inventors have developed a new technique which uses polymer technology to polymer coat that part of the endotracheal/tracheotomy tube which comes in contact with the tracheal/subglottic mucosa and with the tracheostoma. The polymer is loaded with anti-inflammatory agents and anti-microbial agents; and programmed to release the drugs locally around the tube at a relatively high concentration, in a controlled and sustained fashion, aiming to decrease the inflammation and infection that occur with prolonged intubation. Tracheotomy tubes typically cause a foreign body reaction with granulation tissue and inflammation, that result in stenosis in the subglottic area, and excessive granulation around the tracheostoma and that segment of the trachea located at the tip of the tube. Endotracheal tubes typically cause inflammation and chondritis at the area in contact with the tip of the tube and the cricoid area. The polymer-coated tube of this invention is programmed to release corticosteroids along with antibiotic continuously throughout the duration of the intubation. This advantage is particularly important in the pediatric population which has a relatively narrow airway and where a minor subglottic inflammation or swelling may lead to significant airway compromise.

The inventors have successfully coated standard endotracheal tubes and tracheotomy tubes made of polyvinylchloride (PVC) with a polymer that is loaded with corticosteroids and with iodine. They have also successfully loaded the polymer as well, with other antimicrobial agents such as cephazolin, gentamicin and tetracycline. They have shown that the drugs are released in a sustained fashion for prolonged periods of time. They have demonstrated that the polymer holds the drugs in storage in an inert and stable fashion for at least two to three years, and will start releasing the drugs only when coming in contact with body fluids or mucosa. The duration and quantity of the release can be programmed at the time of the coating to last up to several months The areas of the tracheotomy tubes that are important to coat are those parts of the tube in contact with the stoma, and that part around the inflatable cuff in contact with the subglottic mucosa, especially the area of the cricoid. Those are the sites where inflammation and granulation tissue typically occur.

In preferred embodiments, this invention involves an endotracheal tube or tracheostomy tube for implantation into the body and coming into contact with body tissue and fluids comprising said endotracheal tube or tracheostomy tube having thereon a biocompatible polymer coating on its exterior surface. Said polymer coating is formed of non-hydrogel polymer and is insoluble in a biological medium and soluble in an organic solvent. Said polymer coating contains effective amounts of an anti-infective agent and/or anti-inflammatory agent. The anti-infective agent and/or anti-inflammatory agent remain effective and are released while the endotracheal tube or tracheostomy tube are implanted into the body. In a special embodiment, the anti-infective agent remains effective while the endotracheal tube or tracheostomy tube are implanted into the body, as well as after they are removed from the body. In specific embodiments, the anti-infective agent is iodine and the anti-inflammatory agent is a steroid, such as dexamethasone. The preferred polymer for coating is polyurethane.

In an alternative embodiment, a tube, catheter or drain is coated with an anti-inflammatory agent which is a member selected from the group consisting of steroidal and non-steroidal anti-inflammatory agents and an anti-infective agent which is a member selected from the group consisting of iodine and antibiotic anti-infective agents.

Specifically, the tube, catheter or drain can be one for implantation into the body and the anti-infective agent and anti-inflammatory agent remain effective and are released over the entire length of time that the device is implanted.

Instead of the tube, catheter or drain containing both an anti-inflammatory agent and an anti-infective agent in the coating as set forth above, the device could contain either one of the anti-inflammatory agent or the anti-infective agent alone in the polymer coating as the active ingredient. If iodine is the active ingredient, the iodine can be matrixed in the coating, complexed in the coating or both complexed and matrixed in the coating.

BRIEF DESCRIPTION OF THE DRAWINGS

FIG. 6a is a view illustrating a typical nasal airway device.

FIG. 6b is a schematic view illustrating the nasal airway device in its inserted position.

DETAILED DESCRIPTION OF THE INVENTION

Figure 1:
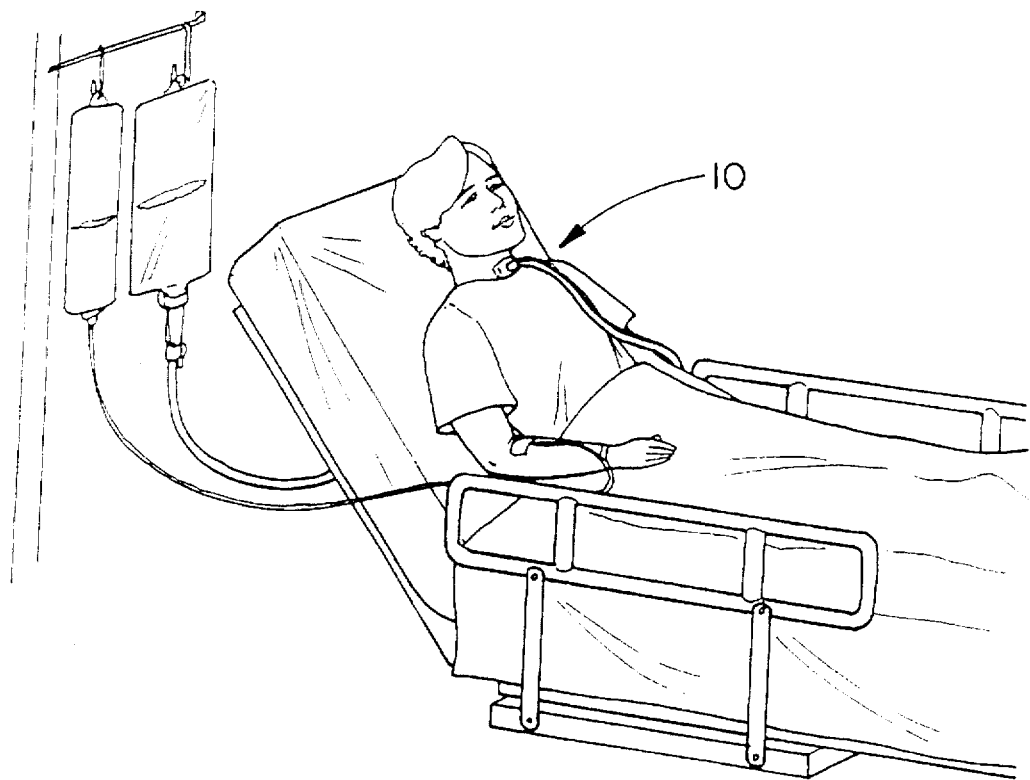
FIG. 1 is a pictorial view illustrating the use of a tracheostomy tube in a patient.

Examples for manufacturing anti-infective/anti-inflammatory coating compositions.

The coating is applied to the surface by dipping or spraying solutions of the polymers containing the active agent dissolved or dispersed in the polymer solution. The solution may contain one or more active agents, either anti-infectives or anti-inflammatories or both. The coating can be a monolayer containing both kinds of agents or can be a multilayer where each layer contains either anti-inflammatory agent or anti-infective agents. The order of the layers depends on the properties of the agent, i.e. potency, chemical reactivity, solubility, diffusibility through membranes, etc. and the order of availability designed for the specific application. For example, if an immediate and short term anti-infective activity is required (1-3 days) and long-term anti-inflammatory effect (several weeks) the inner coating will be of only the anti-inflammatory effect (several weeks) the inner coating will be of only the anti-inflammatory agent in a non-complexing iodine polymer, i.e. ethylenevinyl acetate (EVAc) and the outer coating will be a polyurethane layer which will be immersed in aqueous or alcoholic iodine solution for iodine complexation on the outer surface.

EXAMPLES

1. The following coating solutions are prepared

The general composition of polymer solutions for coating are:

| A. antifungal + antibacterial | |
|---|---|
| Polymer | 0.2–5 g |
| Antifungal | 0.01–1 g |
| Antiinfective | 0.01–1 g |
| Solvent | to 50–500 ml |
| B. antibacterial | |
| Polymer | 0.2–5 g |
| Antiinfective | 0.01–1 g |
| Solvent | to 50–500 ml |
| C. antiinflammatory + antibacterial | |
| Polymer | 0.2–5 g |
| Antiinflammatory | 0.01–1 g |
| Antiinfective | 0.01–1 g |
| Solvent | to 50–500 ml |
| D. antiinflammatory | |
| Polymer | 0.2–5 g |
| Antiinflammatory | 0.01–1 g |
| Antiinfective | 0.01–1 g |
| Solvent | to 50–500 ml |
| E. blank—no actives | |
| Polymer | 0.2–5 g |

-continued

| Solvent | to 50 ml |

Typical polymers are: Polyurethane, ethylenevinyl acetate, silicone dispersion

Typical antiinfectives are: Iodine, aminoglycosides (gentamicin, tobramicin), ciprofloxacin, parabens, quaternary ammonium salts (benzalkonium chloride), chloramphenicol.

Typical antifungals are: Amphotericin B, Nystatin, Clotrimazol. Typical anti-inflammatories are: Dexamethasone, triamcinolone, hydrocortisone, baclomethasone, indomethacin, ibuprofen, naproxen Typical solvents are: dichloromethane, chloroform, ethanol, tetrahydrofurane, acetone (a solvent that dissolves the polymer and dissolves or disperses the drug and it is compatible with the device to be coated).

The coating schedule can be: coating C only; coating D over coating B; coating A over coating D, etc.

Typical examples

| A. antifungal + antibacterial | |
| --- | --- |
| Ethylene vinyl acetate (40% hydrolyzed) | 1 g |
| Nystatin (antifungal) | 0.1 g |
| Proplparaben (general antibacterial) | 0.05 g |
| Dichloromethane | to 50 ml |
| B. antifungal + antibacterial | |
| Ethylene vinyl acetate (40% hydrolyzed) | 1 g |
| Amphotericin B (antifungal) | 0.1 g |
| Ciprofloxacin (antibacterial) | 0.1 g |
| Dichloromethane | to 50 ml |
| C. antimicrobial | |
| Polyurethane | 2 g |
| Iodine | 0.6 g |
| Dichloromethane | 50 ml |
| D. antifungal + antiinflammatory | |
| Ethylene vinyl acetate (40% hydrolyzed) | 1 g |
| Nystatin (antifungal) | 0.1 g |
| dexamethasone | 0.1 g |
| Dichloromethane | to 50 ml |
| E. antiinfective + antiinflammatory | |
| Polyurethane (Plletane) | 1 g |
| Nystatin (antifungal) | 0.1 g |
| dexamethasone | 0.1 g |
| Dichloromethane | to 50 ml |

Example 2

Coating of catheters or tubes: An intravenous catheter is dipped once in solution A and dried at room air to form a uniform coating of 0.01 mm thick. A second dipping in solution D providing a total coating thickness of 0.016 mm.

In a similar way, the catheter or tube is dipped in solution D only.

In a similar way, the catheter or tube is dipped in solution E only.

In a similar way, the catheter or tube is dipped in solution A and then in solution C.

The examples set forth above are exemplary. These amounts can be increased or decreased depending on clinical necessity. Conditions such as patient sensitivity, length of time the device will be inserted and severity of potential infection are examples that those skilled in the art will take into consideration in creating an optimally effective device.

The same technology employed for coating catheters is employed to coat tracheostomy tubes, endotracheal tubes, oral airway devices, nasal airway devices and other intubation devices.

In general, the invention contemplates the coating of a medical device for implantation into tissue or insertion into a body orifice. These devices are exemplified by tracheotomy tubes, endotracheal tubes, tracheal tubes, laryngeal/bronchial stents, laryngeal oral airway devices, keels, esophageal reconstruction tubes, nasal/paranasal tubes, nasogastric tubes, ear ventilation (PE) tubes, gastrostomy tubes, foley catheters, intravenous catheters and all kinds of indwelling percutaneous catheters used for long-term delivery of intravenous fluids and for long-term bladder intubation.

While iodine is the preferred antiinfective agent, other antiinfective agents are seen to be useful. Antibiotic antiinfective agents are exemplified by aminoglycosides, penicillins, cephalosporins, polymyxin, ofloxacillins, gentamycin, cephazolin, clindamycin, aminoglycosides, tetracyclines and their analogs.

Exemplary antifungal agents are nystatin, griseofulvin, lotrimin, mycostatin, ketoconazole, amphotericin B and analogs thereof. Antiviral agents include idoxuridine, amantadine, vidarabine, interferon, acyclovir, and analogues thereof.

Anti-inflammatories that can be incorporated into the polymeric coatings include steroids and non-steroidal anti-inflammatories. For example, the corticosteroids can be dexamethasone, hydrocortisone, triamcinolone, methylprednisolone or analogs thereof. Non-steroidal anti-inflammatories include compounds such as cyclosporin, indomethacin, ibuprofen, and naproxen.

Auxiliary compounds such as anti-thrombogenic or anti-coagulant drugs such as heparin, prostaglandins and warfarin may be added to the polymer coating composition. Anesthetics, such as lidocaine can also be added to the coating composition as an auxiliary agent to decrease pain.

While one could use any of the corticosteroids, the choice of the antimicrobial is more difficult. One should use an antimicrobial that is capable of inhibiting resistant microorganisms that grow as a "superinfection" due to prolonged exposure to the antibiotic. While bacteria ultimately develop resistance to any of the antibiotics, there is no known germ resistant to iodine, which is a universal antimicrobial agent. Iodophors have long been used as both antiseptics and disinfectants. Published reports on iodine demonstrate that in addition to being viricidal, it is bacteriocidal, mycobacteriocidal, and if left in contact for long enough, fungicidal and sporicidal (spores). Iodine solutions or tinctures have long been used by health professionals, primarily as antiseptics on skin or tissue. Iodine is able to penetrate the cell wall and nucleus of microorganisms quickly, and it is though that the lethal effect results from disruption of protein and nucleic acid, structure and synthesis. It is important to keep in mind, however, that the final result of a particular biocidal procedure is dependant not only on the intrinsic sensitivity of the organism to the chemical agent, but also, more importantly, on the length of exposure to the antiinfective agent. In other words, the longer the exposure to the iodine, for example, the more effective will be germ inactivation.

It is essential that the polymer be selected based on its adherency properties to the specific surface materials. In general, surfaces of a certain polymeric material should be coated with a similar polymeric material which fits the requirements listed above. Examples of polymers which are effective coating agents are polyurethane, ethylenevinyl acetate and silicone dispension.

Characteristics of the polymers, iodine concentrations and rates of release

The thickness of the polymers could be varied from 0.001 inch to several millimeters. This variation in thickness results in different concentrations of free iodine being released, varying from 0.01% mg iodine/mg polymer (wt/wt), to 40% mg iodine/mg polymer (wt/wt). This results in a range of iodine release that can hence be adjusted. Other than varying the thickness of the polymers and the amount of drug incorporated wt/wt, another method has been used to program the amount of iodine released. This second method consists of applying a second coat of polymer over the first coat. The first polymer coating is typically a polymer-iodine complex which released the iodine via a desorption mechanism. The second coat is either a polymer-iodine matrix which releases iodine slowly by diffusion, or an empty polymer (one free of medicament) through which the iodine from the first coating permeates. This second coat results in a controlled sustained release of the iodine in a fashion that is programmable. More than two layers of polymers may also be added as the coatings.

To prepare the polymer/iodine matrix, solid elemental iodine is dissolved into a solution of the polymer; the polymer/iodine matrix is then formed onto the surface of the entubation device by spraying, dipping or painting the surface with the polymer/iodine matrix solution. To prepare the polymer/iodine complex a solution of iodine is applied to a polymer coated tube, e.g., the polymer coated tube is dipped into the solution of iodine.

The polymer coatings are formed by methods known to those skilled in the art, such as solvent casting or melting, spraying or brushing. These coatings are preferably between 1.0 and 0.01 mm in thickness. The polymers should be biocompatible and non-erodible. Examples of suitable polymers include ethylene vinyl acetate, polyurethane, silicones, hydrogels, and polyvinyl chloride. In the preferred embodiments, the coatings are uniform and transparent, smooth and very thin (<0.1 mm), and adhere very well to the surface of the device after implantation in vivo and longer term immersion in fluids. The methods set forth herein or similar methods to those set forth can be used to form all or part of devices incorporating drugs such as antiinfectives, anti-inflammatories, anesthetics and anticoagulants. The drugs to be released can be incorporated at the time of manufacture or subsequently, by absorption.

The biologically active agent to be released is incorporated at the time of casting, melting, dipping, spraying, brushing or subsequently, by absorption, with both the coatings and the devices, in whole or in part. The process should yield a polymer releasing the incorporated agent over a prolonged period of time, greater than one day and extending up to several days or weeks Release is a function of diffusion of the agent from the polymeric matrix, and varies by size, concentration and solubility of the agent, as well as by thickness and chemical composition of the polymeric matrix.

Devices are provided having a polymer coating incorporating compounds inhibiting inflammation, infection and subsequent tissue growth onto and around the device. Preferred embodiments include catheters, tubes, and implants for use in the naso-oto-pharyngeal areas of the body where localized chronic infection/inflammation of the tissues surrounding the implant may be decreased by sustained release of antibiotics, antifungals, antivirals and anti-inflammatories.

In a particularly preferred embodiment, polymers incorporating steroids are coated onto devices including tracheal T-tubes, stoma stents, laryngeal/bronchial stents, laryngeal keels, and nasogastric tubes. Corticosteroids/antibiotics combination, administered from the polymer coating at the onset of injury (i.e., time of intubation) and throughout the duration of the intubation seems to prevent the development of subglottic stenosis. The drug-loaded loaded polymer provides a sustained release of steroids and antibiotics locally, at a relatively high concentration in that area which is critically affected.

In yet another embodiment, antifungal drugs are incorporated into the polymer for the treatment of fungal sinusitis, thereby minimizing the relatively high incidence of side-effects that occur when systemic anti-fungal drugs are administered. Antiinflammatory and antiinfective drugs are incorporated for the treatment of chronic bacterial sinusitis. An esophageal silicone stent coated with a film of polymer can be used to provide a site-specific controlled release of corticosteroids and antibiotics for the treatment of caustic injury to the esophagus. Coating that part of the stent, which is in contact with the mucosa, with the drug-loaded polymer provides a sustained release of steroids and antibiotics locally, at high concentration, in the area which is critically affected. This coating achieves the same effect as the systemic administration of the drugs, without side-effects, during the period of intubation. This stent is generally removed at the end of the three weeks.

Coating with or manufacturing the inner flange of a PE tube (the side within the middle ear) a polymer that releases corticosteroids and antibiotics provides a sustained local treatment, decreasing the severity and frequency of the otorrhea.

The coating technology herein disclosed is applicable to devices for insertion into a body orifice, such as tracheostomy or endotracheal tubes, as well as catheters.

Referring now to FIG. 1, a tracheostomy tube 10 is inserted into the trachea of a patient. Other devices intended for insertion into the body through a natural body orifice or a surgically created orifice can be coated with the compositions of this invention. Examples of these devices are a venous catheter, a bladder-foley catheter, an endotracheal tube, a tracheotomy tube, a nasal gastric tube, a closed suction drainage device, a penrose drain, a nasal stent, an ear ventilation tube, oral airway, nasal airway and similar devices inserted directly through the skin of a patient or into a body orifice.

The tracheostomy tubes and insertion devices of the present invention, are standard intubation devices which have biocompatible, non-hydrogel polymer coating(s) 11, 12 and 13 thereon (FIGS. 9a–9d). Commonly, these insertion devices are fabricated from a plastic material.

Figure 2A:
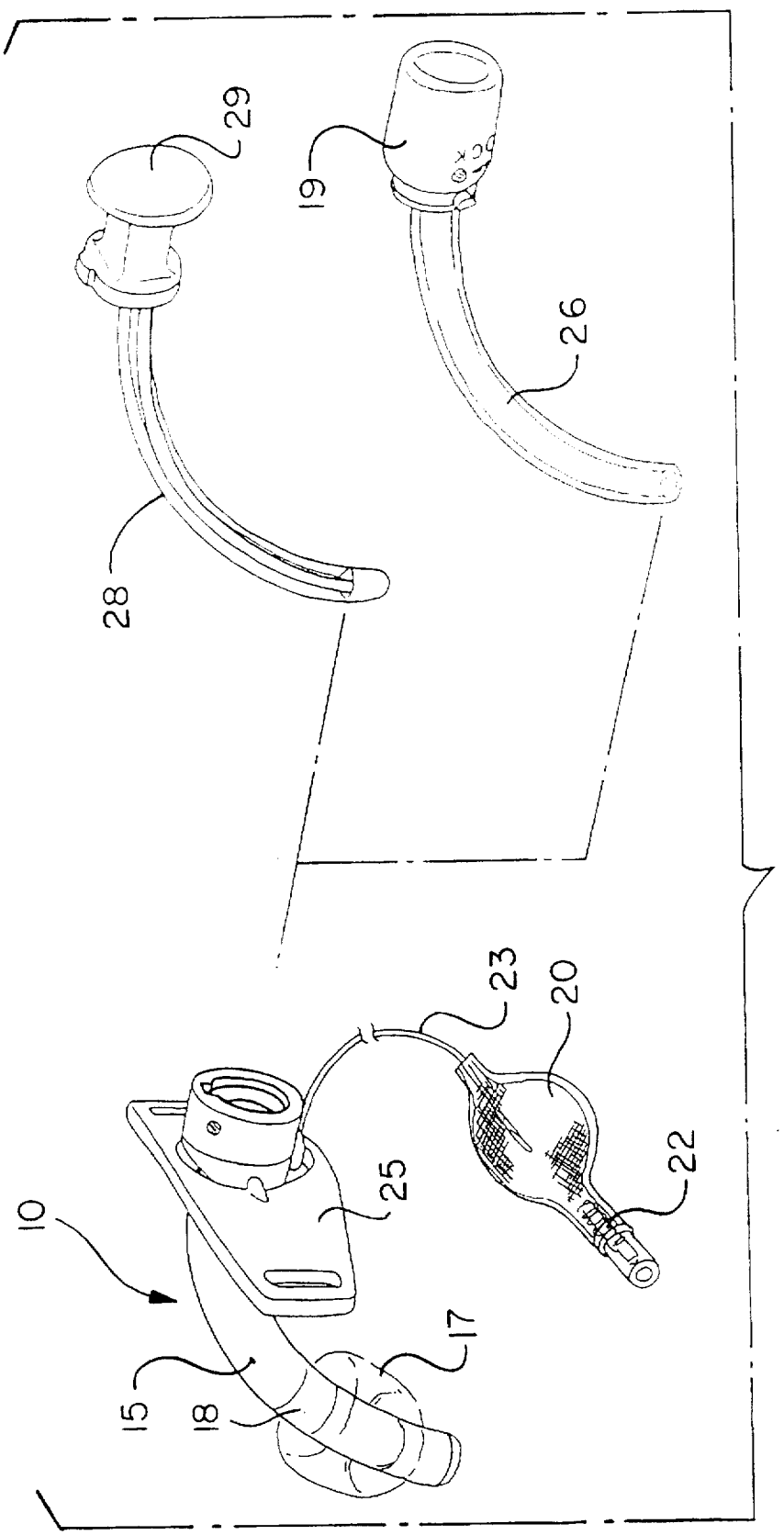
FIG. 2a is an exploded pictorial view of the components of a typical tracheostomy tube.
Figure 2B:
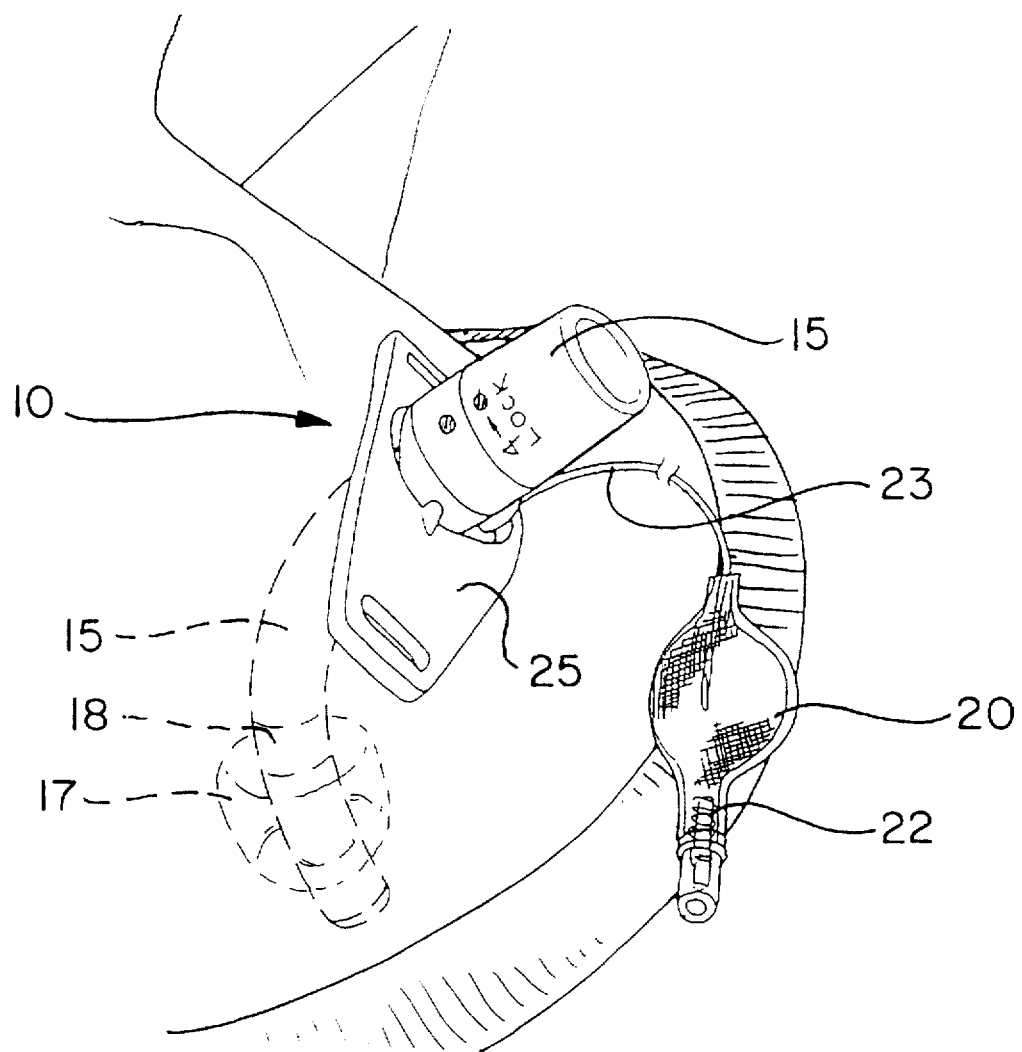
FIG. 2b is a perspective view illustrating inserted tracheostomy tube. The dashed lines represent the inserted coated part of the tube.

With reference to FIG. 2a, the main components of the tracheostomy tube 10 (model shown available from Shiley A. Phizer Company®) are the outer cannula 15 (shown inserted and described by broken lines (FIG. 2B) has an inflatable pressure cuff 17 attached by sleeves 18 to the outer cannula 15. A pilot balloon 20 with a luer valve 22, and attached tubule 23 are used to inflate the cuff 17 surrounding the outer cannula 15. A swivel neck plate 25 insures proper placement of the tube 10 in the trachea. An inner cannula 26 is inserted into the outer cannula 15 for airway management. An obturator 28 is inserted holding handle 29 into the outer cannula 15 when needed as a seal.

Figures 3A, 3B:
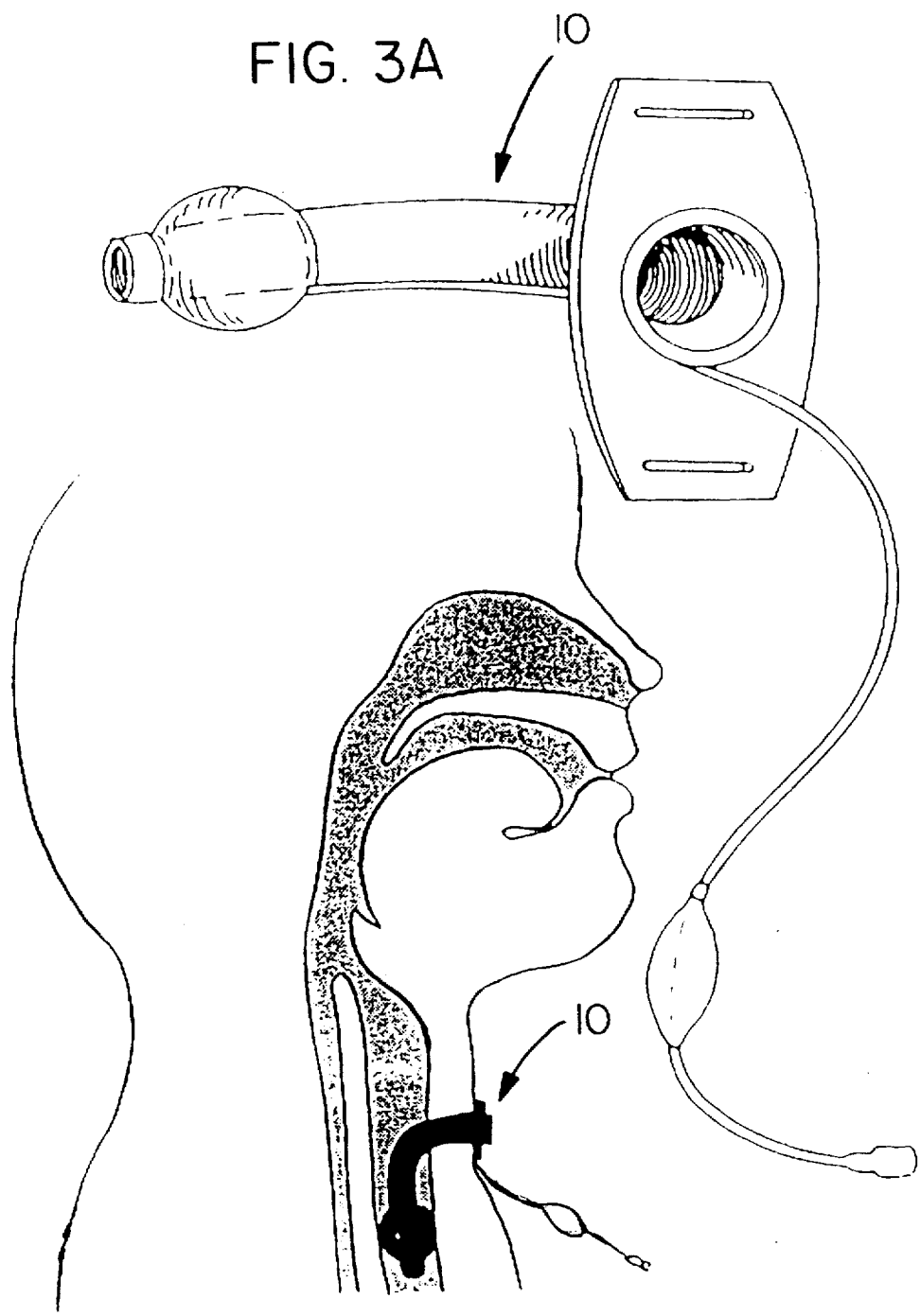
FIG. 3a is a view illustrating a typical tracheostomy tube.
FIG. 3b is a schematic view illustrating the inserted position of the tracheostomy tube.
Figures 4A, 4B:
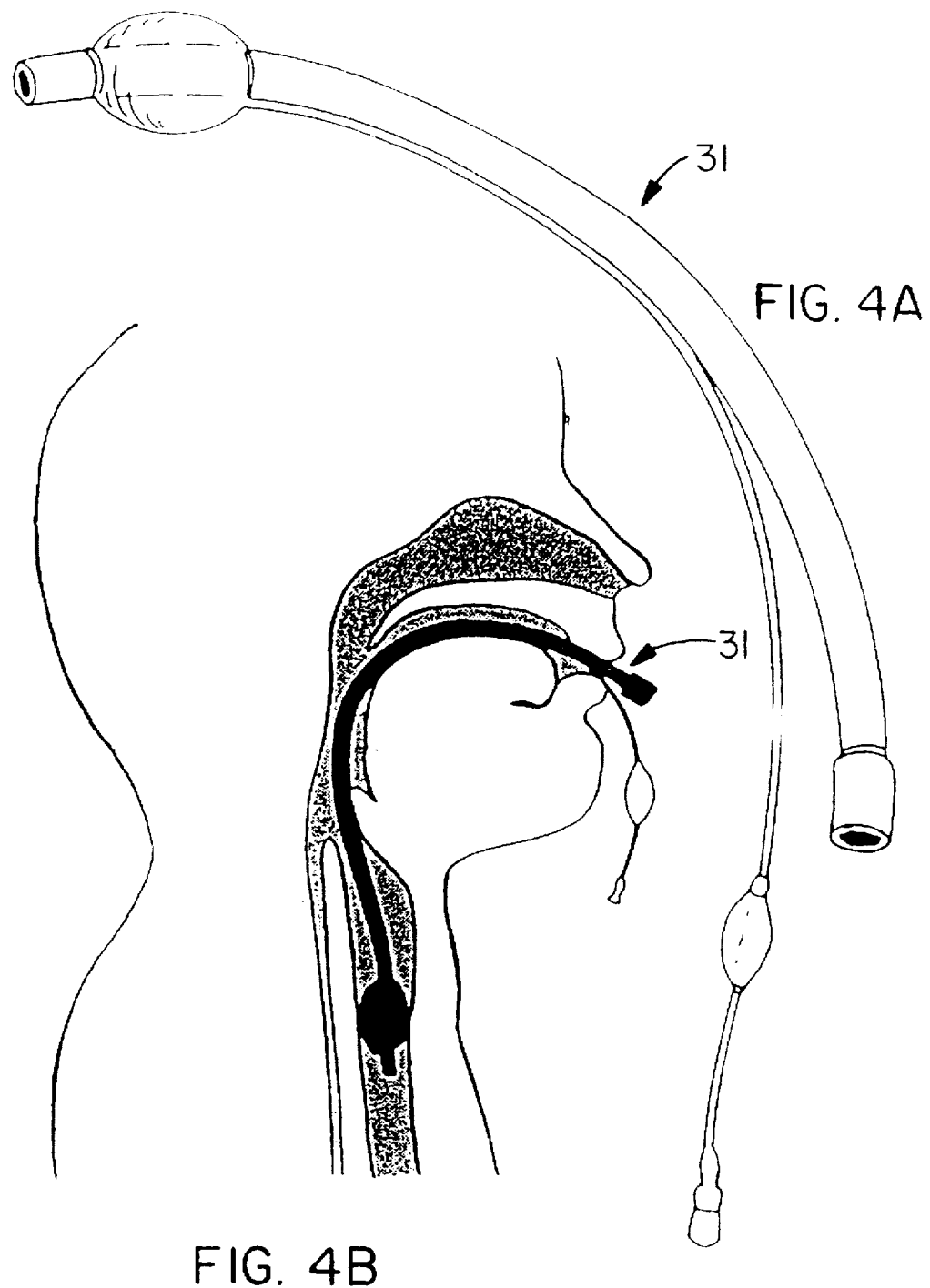
FIG. 4a is a view illustrating a typical endotracheal tube.
FIG. 4b is a schematic view illustrating the inserted position of the endotracheal tube.

In using the tracheostomy tube, the outer cannula 15 is inserted through an incision in the neck leading to the trachea (FIGS. 1 and 3b). After the tube outer cannula 15 is in place, the obturator 28 is to be removed and replaced with the inner cannula 26 and locked in position using lock 19. The outer cannula 15 should be used with the inner cannula 26 in place.

Once the outer cannula 15 is in place, the cuff 17 is inflated by injecting air into the luer valve 22 of the inflation line or tubule 23 using a syringe (not shown). Proper inflation of the pressure cuff 17 is indicated by inflation of the pilot balloon 20. The pressure cuff 17 insures a positive seal between the cuff 17 and tracheal wall (not shown).

FIGS. 3-6 are representative of devices which can be coated with the medicated polymer coatings of this invention. The tracheostomy tube 10 (FIG. 3a) is inserted into the trachea (FIG. 3b). Referring to FIGS. 4a and 4b, an endotracheal tube 31 (4a) is shown positioned through the mouth and into the trachea. An oral airway device 33 (FIG. 5a) is orally inserted (FIG. 5b) and a nasal airway device 35 (FIG. 6a) is nasally inserted (FIG. 6B). Regarding each one of these devices, the important thing to remember is that the part of the device coming into contact with body fluids is to be coated to release medicament into body fluids around the inserted device.

Figure 7:
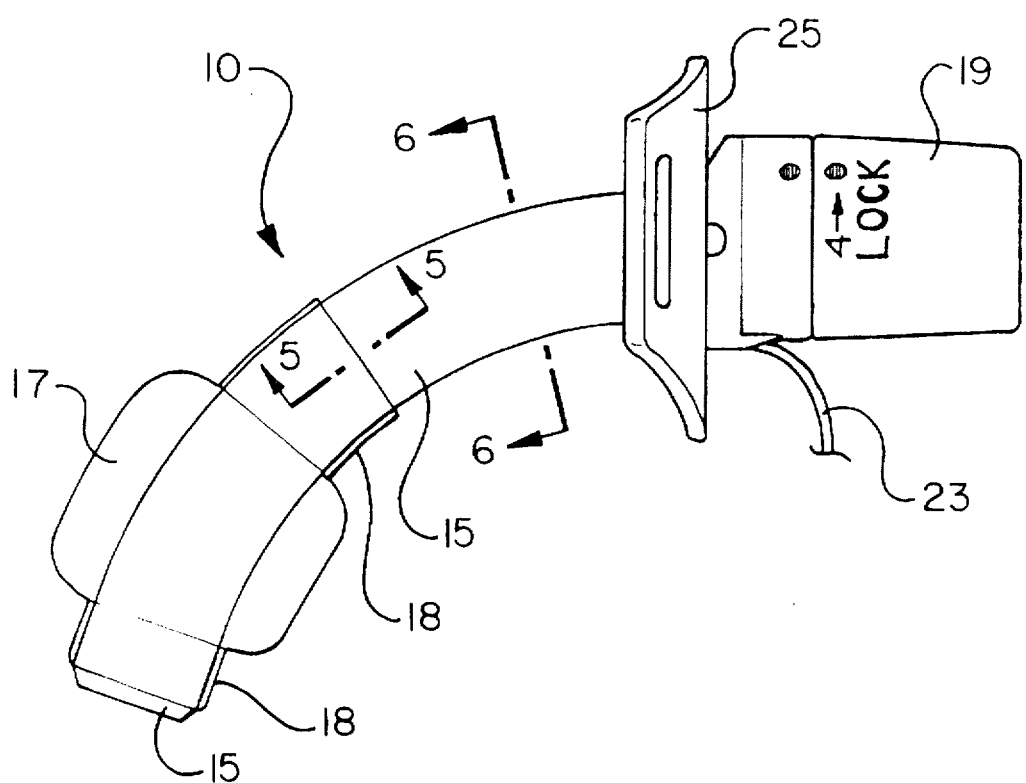
FIG. 7 is an enlarged side elevational view of a typical tracheostomy tube. The coating has been eliminated for ease of illustration.
Figure 8:
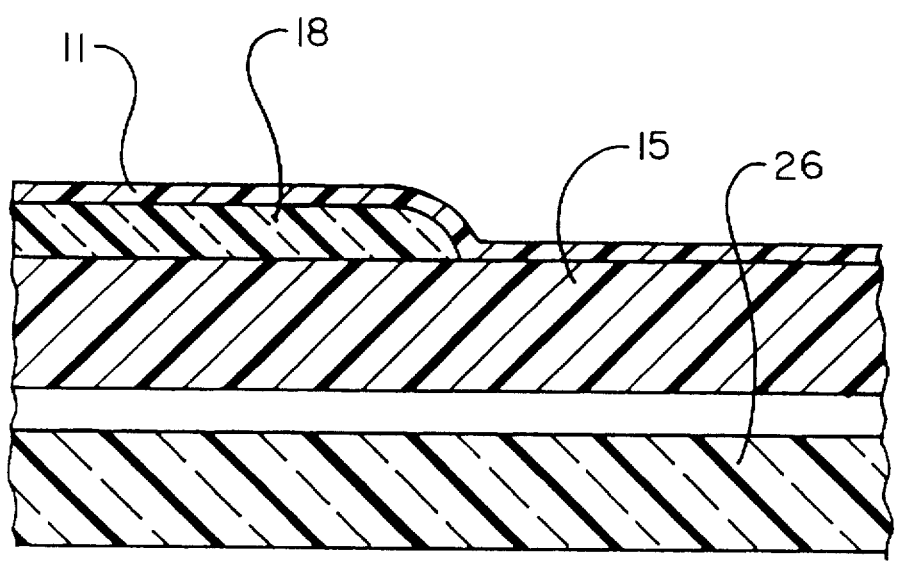
FIG. 8 is a greatly enlarged cross-sectional view thereof taken along lines 5—5 of FIG. 7. The figure is not drawn to scale to more clearly show the coating on the tube.

With reference to FIGS. 7-9, the coatings are applied to the outer surface of the tube 10.

With reference to FIG. 7, the tracheostomy tube 10 has a coated surface. The coatings are illustrated in FIGS. 8 and 9a-9d.

The tracheostomy tube 10 of this invention (FIGS. 9a-9d) has coatings 11, 12, 13 on the surface and the outer cannula 15, as well as the inflatable cuff 17, and its sleeves 18. An inner cannula 26 is inserted into the outer cannula 15. The inner cannula does not come in contact with body fluids and is not coated.

Figures 5A, 5B:
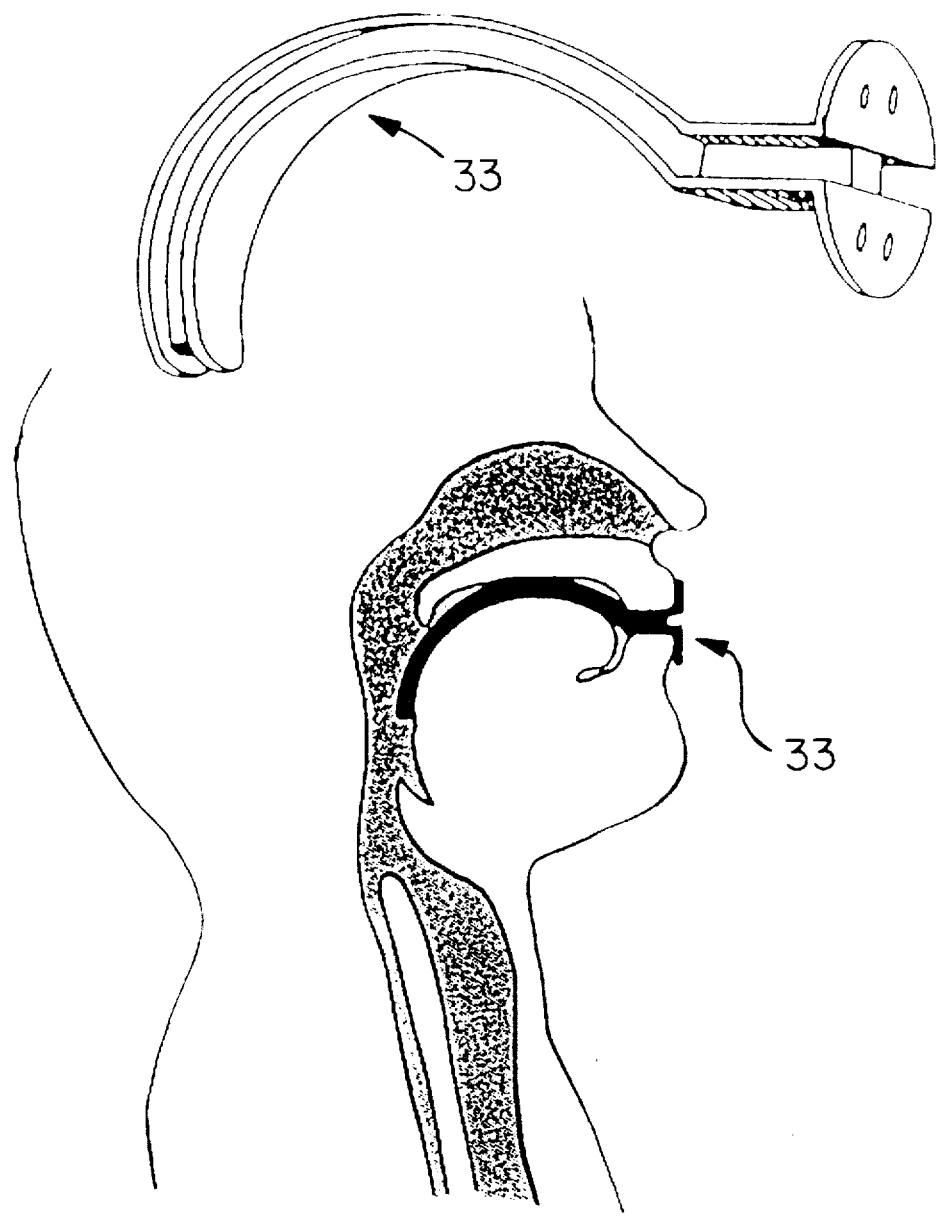
FIG. 5a is a view illustrating a typical oral airway device.
FIG. 5b is a schematic view depicting the oral airway device in its inserted position.

While the emphasis of this invention is directed to endotracheal tubes and tracheostomy tubes (FIGS. 2a and 3a), the inventive coatings herein disclosed can be applied with equal efficiency to oral airway devices (FIG. 4a) and nasal airway devices FIG. 5a. Regarding the coating of these devices, the key feature to be remembered is the fact that these devices when inserted into the body come into contact with body fluids causing the active medicinal ingredients of the coating to dissolve into the body fluids and thereby produce its therapeutic effect.

In order to avoid the problems of infection discussed above, the polymer coating(s) 11 and 12 have elemental iodine complexed or matrixed, respectively, therein (FIGS. 9a-9d). Water in the fluids that are naturally present in the patient's body contact the iodine, dissolving the iodine from the coating(s) 11 and 12. In this manner, a programmable sustained and/or (controlled) immediate release of the iodine from the coating(s) 11 and 12 respectively, is provided.

It is noted that the polymer-iodine coatings 11 and 12 of the present invention provide localized delivery of iodine at relatively high concentrations in the immediate area which is critically affected. The released iodine is then available to kill and/or otherwise inhibit the microbe, including bacteria and viruses, that can result in infection. The release of the iodine from the coatings 11 and 12 is programmable, so that release may occur either immediately and/or in a controlled, sustained manner over a prolonged period of time ranging from a few minutes to several weeks or longer.

Pursuant to the teachings of the present invention, the polymers used in the coatings 11, 12 and 13 employed in the present invention exhibit the following traits: (1) the polymers are soluble or dispersible in solution in order to be disposed onto the outer surface of the outer cannula 15 of tube 10 (in this regard, it is noted that thermoplastic and cross-linked polymers that are insoluble are not useful); (2) the polymers do not chemically react with iodine; (3) the polymers are compatible with iodine, so as to form a uniform, solid complex or matrix with the iodine; (4) the polymers are capable of adhering to the surface of the catheter 10; (5) the polymers are capable of forming a uniform coating on the surface of the tracheal tube 10; and (6) the polymers are capable of forming polymer-iodine complexes and matrixes which remain stable during storage, use and disposal thereof without significant loss of iodine for its intended purpose.

All of these polymers are biocompatible, so as to not cause or result in adverse reactions in the patient's body. Furthermore, all of these polymers are nonbioerodible, so that they are not inadvertently released into the patient's body. The polymers are insoluble in water and/or body fluids and remain bound to the surface of the intubation device even after the iodine in the respective coatings has been released. The polymers of the present invention are non-hydrogel insofar as the polymers swell only slightly when in contact with water. This is distinguished from polymers such as polyvinyl alcohol and polyurethane diacrylate which, after exposure to water, may swell up to 100% of the volume prior to exposure to water. This consideration is one factor which permits multiple coatings of the present invention as will be described. A polymer which swells cannot be used in the present invention as a base for another polymer to be coated over the base coating. The polymers preferably have a molecular weight of more than 1,000.

In this manner, the polymers of the present invention are distinguishable from previous coatings such as the polyvinyl alcohol coating of Rosenblatt (U.S. Pat. Nos. 4,381,380 and 5,156,164) which is water soluble and is removed from the surface of a device by dissolution when in contact with body fluids. Also, the referenced coatings are not soluble in organic solvents so a permanent coating cannot be formed from an organic solvent. The present invention also differs from the hydrophilic material of Walker (U.S. Pat. No. 4,994,047) which swells when contacted with an aqueous liquid.

The polymers utilized in the iodine complexed coating 11 is preferably polyurethane or polyurea. The polymers utilized in the iodine matrixed coating 12 is selected from the group consisting of polyurethane, ethylene vinyl acetate, polyvinylchloride, polyesters, nylon, polycarbonate, polyethylene, polymethyl methacrylate, cellulose esters (like ethyl, methyl and propyl), polypropylene, polystyrene, polytererefluoroethylene, polyvinylchloride, poly (ethylenevinyl acetate), elastomeric organosilicon polymers, poly(hydroxy alkyl esters), copolymers and combinations thereof.

Preferably, the coatings 11, 12 and 13 are between 0.01 and 1.0 mm in thickness and, most preferably, between 0.1 and 0.22 mm in thickness.

The polymer coatings may be formed by solvent casting or melting. The polymer coatings 11, 12 and/or 13 are applied to the surface by dipping, spraying, brush coating, or any other suitable method.

The iodine utilized herein is elemental iodine. As will be discussed at greater length below, the iodine may be incorporated into the polymer coatings 12 and 11 either by matrixing at the time of manufacture (casting or melting), or subsequently thereto, by complexing such as by absorption therein to obtain a solid solution of the iodine. The solid solution is a mixture or distribution of iodine molecules within the polymer chains. This solid solution is differentiated from a physical mixture of iodine particles dispersed in the polymer.

In the tracheal tubes 10 of the present invention, the polymer/iodine complexes 11 (FIG. 9a) are formed by complexing the iodine with the polymer coating after the polymer coating has been applied to the outer surface of the tube 10. This can be achieved by spraying, dipping or painting an iodine solution on the outer surface of the tube 10 that already has the polymer coating thereon. Iodine release occurs by decomplexation or desorption of the iodine as a result of an equilibrium between the polymer coating 11 and the surrounding medium. Since iodine in a polymer-iodine complex may be easily contacted and dissolved by the water in the body's natural fluid, the release of complexed iodine from the iodine-polymeric coatings 11 of the present invention occurs relatively fast (within several minutes). Iodine can be complexed and loaded by immersing the polymer-coated device in an iodine solution in water or alcohol. The kind of polymers that are capable of complexing iodine are those that contain urethane or urea bonds. Complexing can be accomplished within 0.03 to 60 minutes and then dried.

In the tubes 10 of the present invention, the polymer/iodine matrixes 12 are formed by dissolving solid elemental iodine into the polymer solution to form the polymer-iodine matrix. The polymer-iodine matrix is then subsequently formed onto a surface of the tube 10 by spraying, dipping or painting the surface with the polymer-iodine matrix solution. The iodine is released from the polymer matrix by diffusion as a result of water penetrating into the matrix, dissolving the iodine and carrying it out into the surrounding medium. Since, it is more difficult (as compared to complexed iodine) for matrixed iodine to be contacted and dissolved by the water in the body's natural fluids, the release of matrixed iodine from the polymeric coating 12 is more sustained than is the release of complexed iodine from the polymeric coating 11.

Figures 9A, 9B:
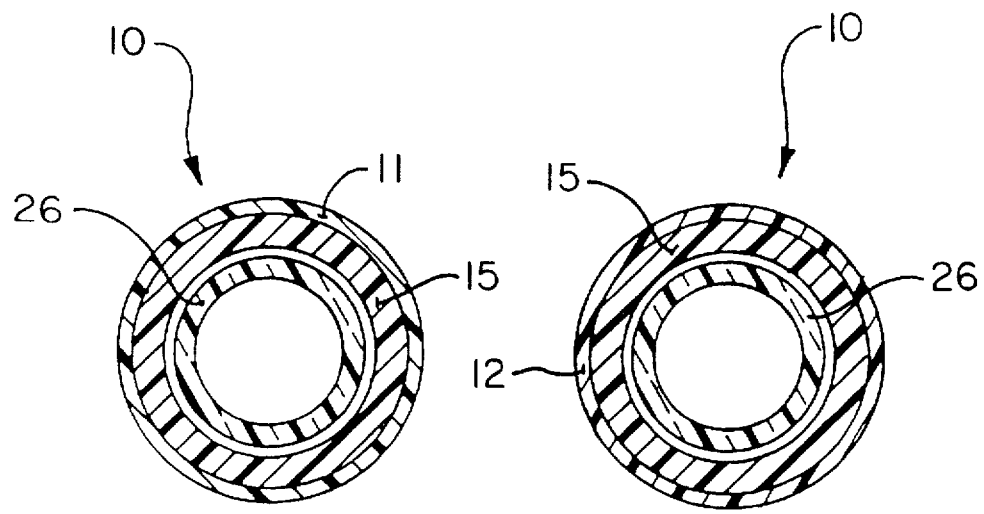
FIG. 9a is a cross-section view of a first embodiment of the present invention (not to scale) taken along lines 6—6 of FIG. 7, wherein iodine is complexed into a polymer coating on the tube for the release of the iodine from the coating to inhibit infection.
FIG. 9b is a cross-section view of an embodiment of the present invention (not to scale) taken along lines 6—6 of FIG. 7, wherein iodine is matrixed into a polymer coating on the tube for the release of the iodine from the coating to inhibit infection.

With particular reference now to FIG. 9a, the first preferred embodiment of the tube 10 of the present invention is illustrated. In the first embodiment, a polymer coating 11 is directly disposed on the outer cannula surface of the tube 10. The polymeric coating 11 has iodine complexed therein. Complexing of the iodine in the polymeric coating 11 means that the iodine may be easily contacted and dissolved by the water in the body's natural fluid for quickly immediately releasing the iodine from the polymeric coating 11. FIG. 9a is not drawn to scale in order to more clearly show coating 11.

The second preferred embodiment of the tube 10 of the present invention is illustrated in FIG. 9b. In this second embodiment, a polymer coating 12 is directly disposed on the outer cannula 15 surface of the tube 10. The polymeric coating 12 has iodine matrixed therein As will be readily understood by those skilled in the art, matrixing (as opposed to complexing) of the iodine makes contact of the iodine with water in the body's natural fluids (contact that would dissolve the iodine) more difficult. In this manner, the release of the iodine from a polymer coating 12 in which it is matrixed, is slower than that of complexed iodine, so that the matrixed iodine release is sustained and controlled. FIG. 9b is not shown to scale in order to more clearly show the coating 12.

Figures 9C, 9D:
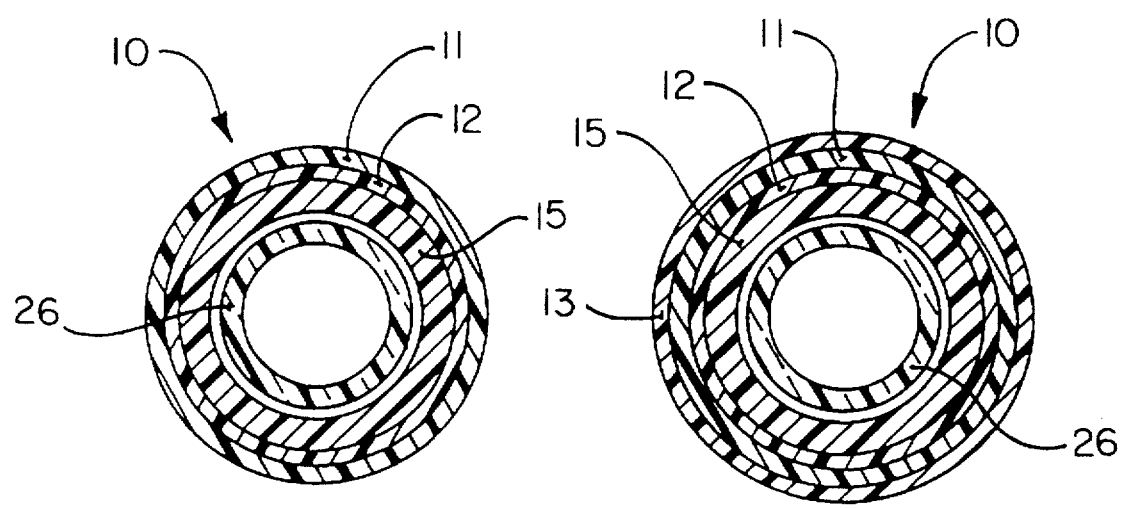
FIG. 9c is a cross-section view of an embodiment of the tube of the present invention (not to scale) taken along lines 6—6 of FIG. 7 wherein iodine is matrixed into a biocompatible, non-hydrogel polymer inner coating on the catheter for the programmable (controlled) sustained release of iodine from the inner coating, and further wherein iodine is complexed into a biocompatible, non-hydrogel polymer outer coating on the catheter for the programmable immediate release of iodine from the outer coating to inhibit infection.
FIG. 9d is a cross section view of another embodiment of the coated tube (not to scale) wherein inner coating and outer coating of FIG. 9C is further coated with a polymer having no iodine therein.
Figure 10:
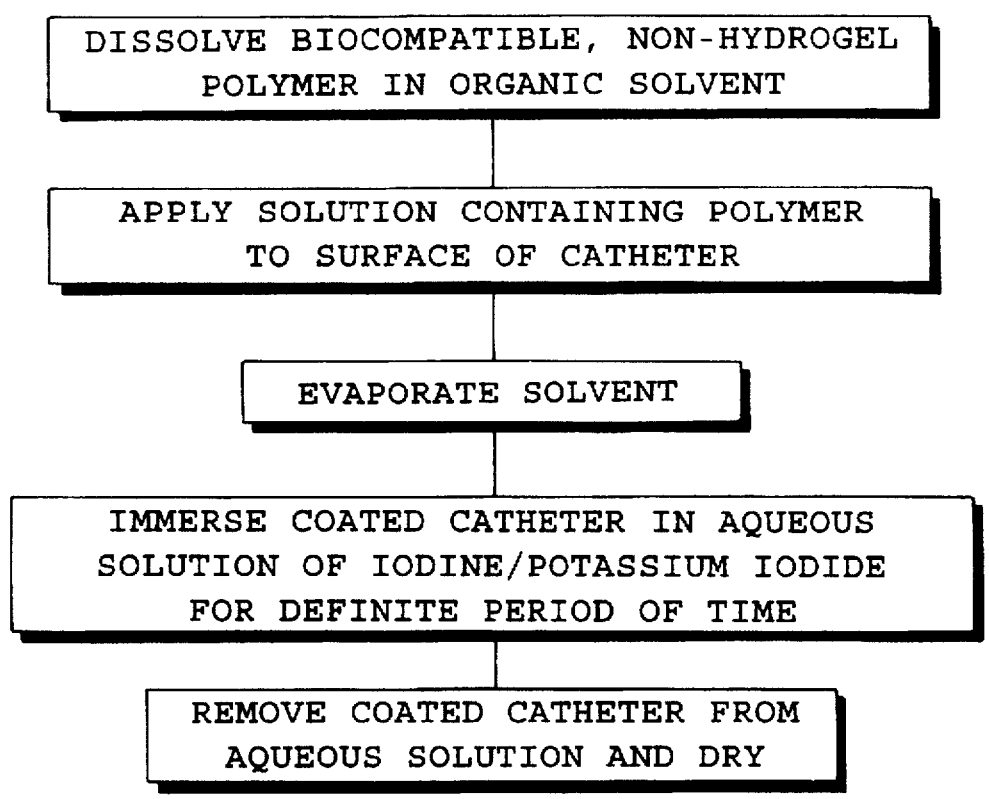
FIG. 10 is a block diagram showing the method of preparing the complexed coating.
Figure 11:
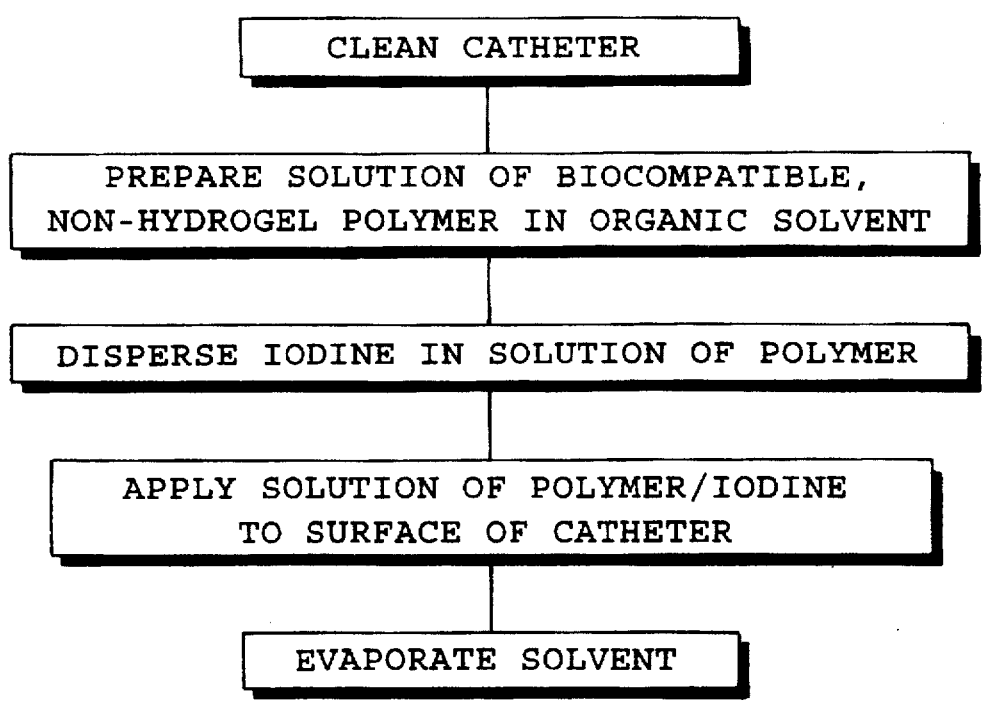
FIG. 11 is a block diagram showing the method of preparing the matrixed coating.
Figure 12:
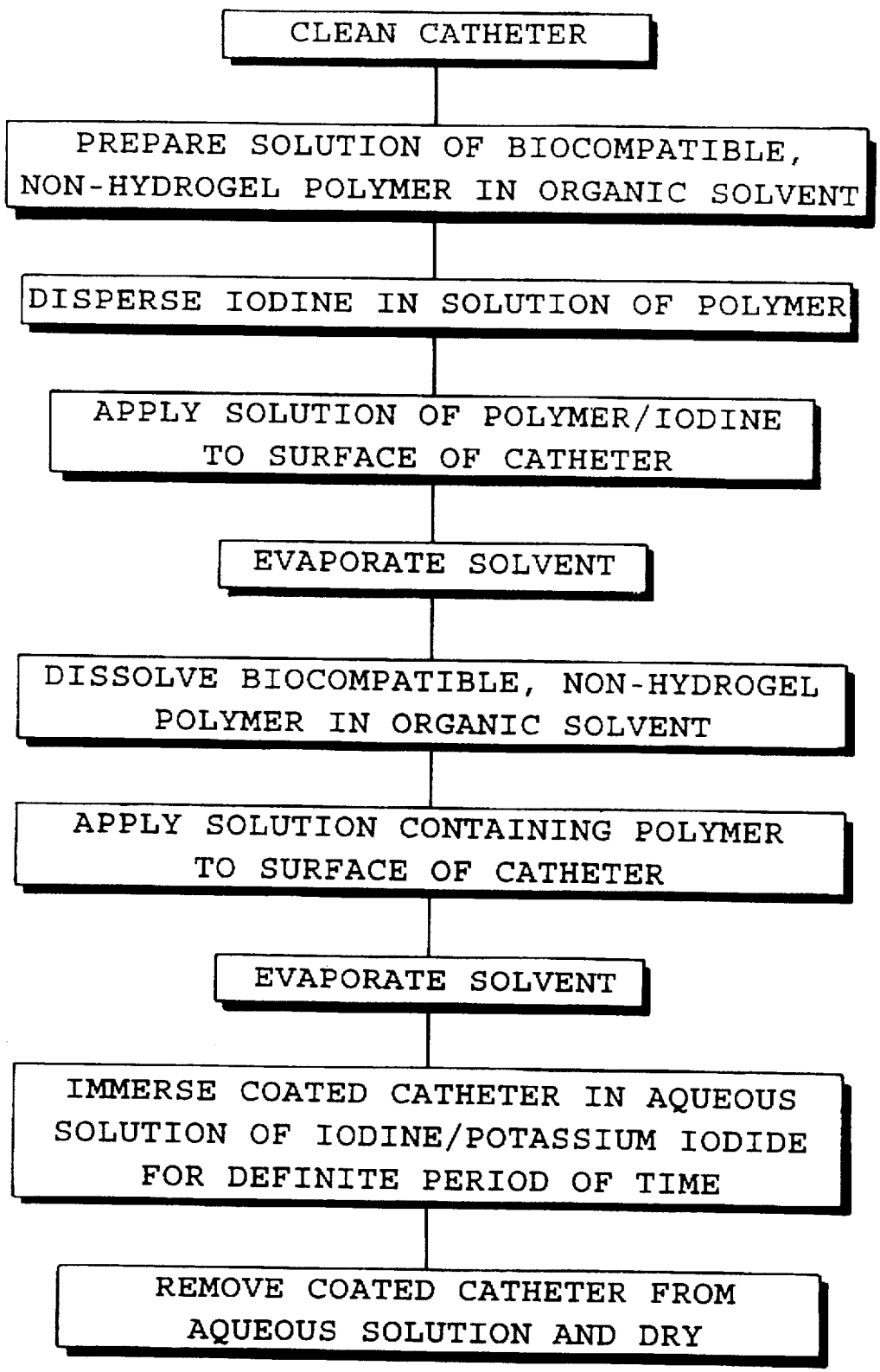
FIG. 12 is a block diagram showing the method of preparing the complexed coating over a matrixed coating.
Figure 13:
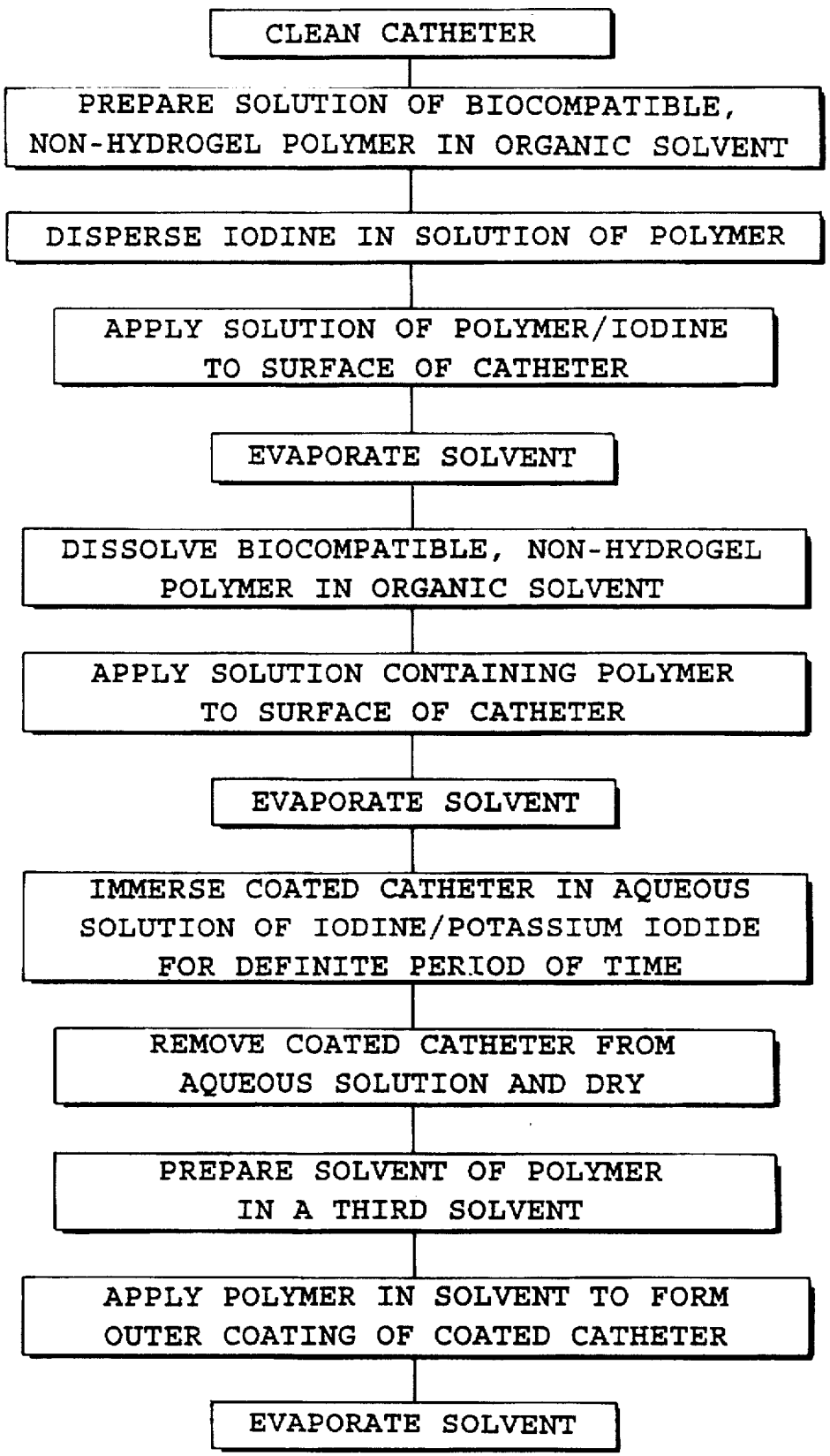
FIG. 13 is a block diagram showing the method of applying a coating without iodine to the coating of FIG. 12.

With particular reference now to FIG. 9c, the third preferred embodiment of the tube 10 of the present invention is illustrated. In the third embodiment, a first, inner polymer coating 12 is directly disposed on the outer cannula surface of the tube 10. The inner polymeric coating 12 has iodine matrixed therein. A second, outer coating 11 is disposed on the inner coating 12. The outer polymeric coating 11 has iodine complexed therein. In this fashion, a two-layer polymeric coating provides both an immediate release from the complexed coating 11, as well as a continuous and sustained release from the matrixed iodine coating 12. FIG. 9c is not drawn to scale in order to more clearly show the coatings 11, 12.

In this regard, it is noted that the presence of the outer coating 11 acts to further shield the iodine in the polymer-iodine matrix of the inner coating 12 from the water in the body's natural fluids. In this fashion, the release of the matrixed iodine from the inner coating 12 is programmed to be further slowed. This feature provides an even greater sustained release of the iodine than is available from the single polymer-iodine matrix coating 12 of FIG. 9b. Thus, infection about coated tube 10 is inhibited over a longer period of time.

Referring to FIG. 9d, if desired, any of the three aforementioned embodiments (FIGS. 9a–9c) of the coated tubes 10 may further include a non-iodized polymer coating 13 disposed on either the complexed coating 11 or on the matrixed coating 12. This non-iodized polymer coating 13 acts to further shield the iodized coatings 11 and 12 from the water in the patient's natural bodily fluids, which contact and dissolve the iodine. In this fashion, the release of the iodine from the coatings 11 and/or 12 may be still further programmed to provide a more precise and sustained release of iodine. The coatings are stable at shelf conditions and will not start releasing iodine until the iodine in the coating comes into it is in contact with body fluids or other fluids. While coating 13 (FIG. 9d) coats both the matrixed coating and complexed coating, it could coat single layer coatings (FIGS. 9a, 9b).

The method steps for carrying out the coating processes are set forth in FIGS. 10–13.

It is noted that the release of iodine is a function of, and varies according to, the thickness, concentration, chemical composition and solubility of the polymer from which the coating 11, 12 or 13 are fabricated. Thus, the variation of any one or all of these factors may be resorted to in order to program the release of the iodine therefrom.

The variation of the polymer coating thickness alters the release of iodine from the polymer-iodine complexes/matrixes, in that the thicker the coatings, the slower and more sustained will be the release of the iodine from the iodine-polymer complexes and matrixes. This is achieved by the fact that thicker coatings make the contact between the iodine and the water in bodily fluids more difficult to achieve. Control of the thickness of the coating can be achieved by subsequent dippings, dipping the device in polymer having higher concentrations of iodine or by spraying/brushing a thicker coating of the polymer-iodine solution on the surface. The initial release rate is approximately constant irrespective of the thickness of the coating. The non-iodized coating 13 may also be viewed as a rate limiting coating. The thicker the rate limiting coating 13, the slower will be release rate of iodine. The time delay increases as the thickness of the rate limiting coating 13 increases.

The variation of the concentration (or loading) of iodine in the polymer-iodine complexes 11 and matrixes 12 alters the release of iodine from the polymer-iodine complexes/matrixes 11/12, respectively, in that the higher the loading of iodine, the more immediate and more sustained will be the release of the iodine from the polymer-iodine complexes 11 and matrixes 12. In this regard, iodine loading varies from 0.01% mg iodine/mg polymer (wt/wt) to 40% mg iodine/mg polymer (wt/wt). The preferred loading value is approximately 0.1% to 25%. To obtain these loading values, the iodine-polymer coating solution is more concentrated with respect to iodine to compensate for evaporation of iodine during the coating process.

Additives may further alter the release profile or shelf life of the polymer-iodine coatings 11 and 12. In this respect, the coatings 11, 12 and 13 may further contain various additives, such as inorganic or organic salts, complexing molecules, such as pyrrolidone derivatives, and natural and synthetic oils. For example, to increase the iodine release rate, a fine powder of potassium iodide (KI) or sodium chloride (NaCl) is added to the polymer-iodine coating solution prior to the coating of tube catheter 10 by dipping or spraying. To retain the iodine in the coating and further slow the iodine release rate, oligomers and polymers such as vinylpyrrolidone, urea and cellulose may be incorporated in the polymer-iodine complexes and matrixes. In this respect, incorporation of such additives aids in making the release of the iodine from the polymer-iodines complexes/matrixes more definitively programmable. A hydrophilic additive, such as polyethylene glycol, increases the release rate since it increases the water penetration into the polymer coating and subsequently increases the leach out of the iodine. In particular, addition of 10% of a polyethylene glycol (PEG 600) decreases the t ½ of an ethyl vinyl acetate coating from 36 hours to 26 hours. If, for example, polyvinylpyrrolidone-iodine complex is used, the release rate will decrease because iodine is complexed and is not free to be released by simple diffusion.

In addition to elementary iodine, the polymer may contain antiinflammatory agents such as steroids and non-steroidal antiinflammatory agents, such as ibuprofen, naproxen and indomethacin, or antibiotics, such as aminoglycosides, penicillins, cephalosporins, polymyxin, ofloxacillins or antifungals such as mycostatic, griseofulvin and ketoconazole. It also may contain anti-thrombogenic drugs such as heparin, prostaglandins and warfarin.

As described herein, coated tracheal tubes, as well as catheters release antiinfective and antiinflammatory agents at various rates depending upon the amount of antiinfective and antiinflammatory agent present and the type of coating employed Extra dip-coatings further prolong the activity of the active ingredient.

The tubes 10 of the present invention will be further understood by reference to the following examples and FIGS. 14–28 which are meant to be illustrative, but not limitative, thereof:

EXAMPLE 1

Polyurethane Coating With Iodine Matrixed Therein

An iodine matrixed polyurethane coating is prepared by dissolving 0.5 grams of iodine crystals in a tetrahydrofuran solution containing 1.5 grams of segmented polyurethane (Estane, TM, Goodrich, Cleveland, Ohio).

Coating is achieved by dipping the catheter in the polyurethane-iodine matrix solution. After solvent evaporation, the resulting dark uniform coating of about 0.2 mm may be further coated with a noniodized Ethylene Vinyl Acetate (EVAc) coating by further dipping the polymer-iodine matrix coated needle or cutting blade in a chloroform solution of EVAc. The resultant EVAc coating of 0.05 mm aids in preventing iodine release from the polymer-iodine matrix coating by sublimation. Alternately a solution of polyurethane in acetone (2 weight %) containing iodine (0.05%) was sprayed over various surfaces using a Sigma Spray kit. The spray formed a thin matrixed coating that adheres to the following surfaces: PVC tubings, polyethylene plastic bags, polyethylene and polyurethane made surgical gloves. All surfaces released iodine in vitro for about 10 hours when immersed in buffer solution pH 7.4 containing 0.05% KI.

EXAMPLE 2

Polyurethane Coating With Iodine Complexed Therein

The catheter is first coated with noniodine loaded polyurethane by the dipping thereof in a tetrahydrofuran solution containing 1.5 grams of segmented polyurethane (Estane, TM, Goodrich, Cleveland, Ohio).

Iodine is then complexed into the polyurethane coating by immersing the coated catheter in a 20% iodine/potassium iodide ($I_2$/KI) solution in water. The impregnated polyurethane-iodine complex coating is then dried in room air.

The resulting polyurethane-iodine complex coating may then be further coated with a noniodized Ethylene Vinyl Acetate (EVAc) by dipping the coated catheter in a chloroform solution of EVAc. The EVAc coating of 0.05 mm prevents iodine release from the polyurethane-iodine complex polymer coating by sublimation.

EXAMPLE 3

Catheters were cleaned and dipped into a 2.5% solution of polymer containing 20% iodine based on the polymer mass. Polyurethane (PU) (Estane), Ethyl Vinyl Acetate (EVAc), and ethylcellulose were used as the polymer coating in tetrahydrofuran (THF), dichloromethane, and ethanol solutions, respectively. A uniform coating that strongly adhered to the catheter surface was obtained with each of the three polymers. The coated catheters were further treated by immersing each of them in a 5% iodine/potassium iodide water solution for additional iodine loading by complexation. The EVAc coated catheter was further coated with a PU iodine free coating by dipping the catheter into a 1% PU in THF. The in vitro release of iodine in a potassium iodide solution was determined at 37° C. and the time for 50% iodine release is given. The total mass increase and iodine content was as follows:

| Coating | Coating mass | Iodine loading | Release time (t 1/2) |
|---|---|---|---|
| ethylcellulose | 6.3 mg | 0.3 mg | 20 h |
| EVAc | 4.5 mg | 0.7 mg | 40 h |
| PU | 5.2 mg | 0.6 mg | 45 h |
| PU + Complex | 5.8 mg | 0.75 mg | 24 h |
| EVAc + coating | 5.3 mg | 0.7 mg | 62 h |

The catheters were loaded with a significant amount of iodine and 50% of the loaded iodine was released within the first two days in vitro. The PU matrix+complexed iodine coating rapidly released the complexed iodine, thus the t ½ was decreased. The EVAc double coated catheter had a longer t ½ because of the second coating which reduces the drug release rate from the coated surface.

The uniodized polyurethane coating absorbed an additional 0.15 mg iodine (about 25%) while the other polymers absorbed negligible amounts of complexed iodine. This experiment demonstrates the utilization of programmable iodine releasing system for catheter surfaces.

EXAMPLE 4

The purpose of this experiment was to evaluate the amount of iodine loaded on the matrix coating as a function of the iodine concentration in the polymer-iodine solution. The amount of polymer-iodine coating was also determined as a function of the number of dippings. To solutions of polyurethane (Estane, Goodrich) or ethylene vinyl acetate (EVAc, 40% hydrolyzed) in tetrahydrofuran (2.5 weight %) iodine crystals were added to form solutions containing 10, 20, 30, and 40 weight % of iodine based on the polymer mass. An endotracheal tube made of PVC (Portex) was dipped once in the solutions to coat an area of 10 cm$^2$. After solvent evaporation at room air for 30 minutes, the coating mass and the iodine loading were determined. The coating mass was determined by weighing the device before and after coating and the iodine loading was determined by dissolving the coating in THF and determining the iodine content by UV at 310 nm. When several dippings were made, the coating was dried for 30 minutes before the next dipping. Typical results are summarized below:

| % iodine in solution | Coating mass (mg) EVAc | Coating mass (mg) PU | % Iodine in coating EVAc | % Iodine in coating PU |
|---|---|---|---|---|
| one dip | | | | |
| 10 | 65 | 70 | 7 | 8 |
| 20 | 56 | 55 | 14 | 13 |
| 30 | 48 | 50 | 18 | 21 |
| 40 | 34 | 37 | 24 | 25 |
| two dips | | | | |
| 10 | 110 | 123 | 7 | 8 |
| 20 | 96 | 92 | 13 | 13 |
| 30 | 80 | 85 | 17 | 18 |
| 40 | 62 | 65 | 22 | 23 |

This data show that the iodine loading is similar for both polymers and EVAc is as good as PU for matrix-iodine coatings. The iodine loading increases with the increase in the iodine concentration in the polymer solution. However, the increase in the iodine loading in the dried coating is not proportional to the iodine content in the polymer solution, but decreases with the increase in iodine concentration. This is explained by iodine evaporation during the solvent evaporation which increases with the decrease in the polymer content in the coating solution. The increase in the coating mass in the second dipping is less than double the amount of the first dipping. This is due to a partial dissolution of the first coating during the second dipping. This decrease in coating mass during subsequent dippings can be minimized when the second coating is made by (1) spraying the polymer-iodine solution which evaporates fast leaving a coating without mass loss; (2) the subsequent coating is made with a polymer solution in a solvent that is a non-solvent for the polymer of the prior coating. For example if the first coating is with THF soluble PU which is insoluble in dichloromethane, the second dipping will be in EVAc-iodine solution in dichloromethane.

EXAMPLE 5

The thickness of the coating which affects the total iodine loading can be determined either by subsequent dippings, dipping the device in higher polymer-iodine concentrations, or by spraying a larger amount of polymer-iodine solution on the device surface. In an experiment a venous catheter inserting sheath made of polyurethane (tube of 10 cm long, 0.3 cm in diameter, total outer surface area approximately 9.4 cm$^2$) was coated on the outside by dipping the device in various concentrations of polymer-iodine solutions. Solutions of EVAc in THF in concentrations of 2.5, 5, 7.5 and 10 weight % containing 20 weight % iodine based on the polymer mass were used for coating. The total coating mass and iodine loading are as follows:

| Polym. Conc. | coating mass (mg) | iodine content (mg) | Coating thickness |
|---|---|---|---|
| 2.5% | 57 | 8 | <0.10 mm |
| 5.0% | 120 | 19 | 0.10 mm |
| 7.5% | 190 | 29 | 0.14 mm |
| 10.0% | 320 | 52 | 0.22 mm (not uniform) |

As seen, increase in the polymer concentration increases the coating thickness and the amount of coating material, as well as the iodine content per coating area. Increase in the polymer concentration increases the viscosity of the polymer and thus more polymer is attached to the catheter surface. The duration of iodine release from these coated devices increases with the increase in the thickness of the coating.

EXAMPLE 6

The rate of release from a coated surface was further shown to be controllable by depositing the polymer/iodine coating on culture cluster plates.

Polyurethane-iodine complex: 24 well culture cluster plates (Costar, Cambridge Mass.) were coated with polyurethane by spreading 50 microliters of polyurethane (PU) solution in tetrahydrofuran (THF, 2.5 weight %) per well. After solvent evaporation, a uniform thin coating of 0.4 mg/cm$^2$ was obtained. To each well 3 ml iodine-potassium iodide solutions were added and allowed to react for 60 minutes at room temperature. The solutions were discarded and the wells were rinsed with deionized water for 10 minutes and left to dry at room air for 24 hours. The iodine concentrations in the solution were 1.0M, 0.1M, 0.05M, 0.01M, and 0.001M; the potassium iodide concentrations were 1.5 times the molarity of iodine in the solutions. For each concentration a total of four (4) wells were used. The total amount of iodine absorbed in the PU-iodine complex was 4, 1, and 0.5 weight % (50, 12 and 5 microgram per well), based on the polyurethane coating, from 1, 0.1, and 0.05M iodine solution, respectively. The 0.01M and 0.001M solutions did not provide detectable amounts of iodine.

Iodine release was studied by adding into the wells 3 ml phosphate buffer pH 7.4 at 37° C., or in 0.01M potassium iodide solution at 25° C. The solutions were replaced frequently with fresh solutions and the iodine concentrations in the solutions were determined by UV absorption at 280 nm.

Figure 14:
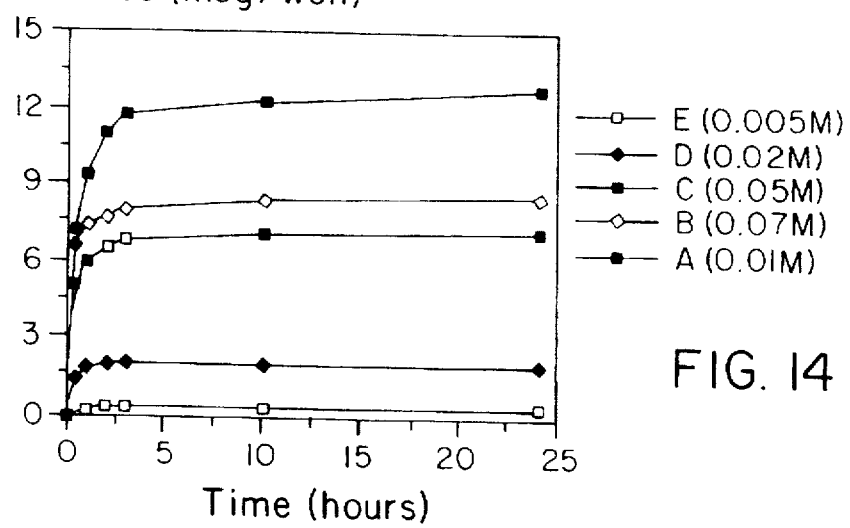
FIG. 14 is a graph of the rate of iodine release from a polymer iodine complex in phosphate buffer.
Figure 15:
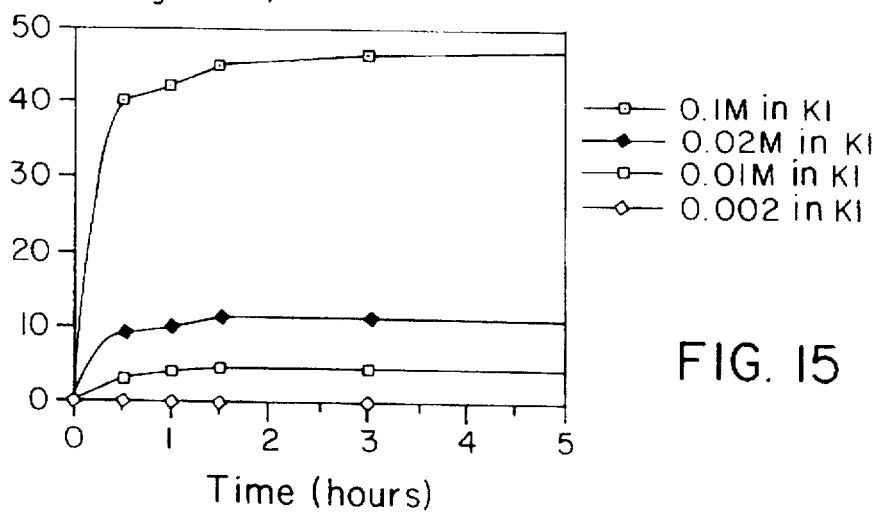
FIG. 15 is a graph of the rate of iodine release from a polymer iodine complex in potassium iodide.

The in-vitro release from polyurethane-iodine complex was rapid both in phosphate buffer and in potassium iodide solution. In phosphate buffer pH 7.4 at 37° C., iodine was released rapidly from the coating with about 90% of the iodine released in 3 hours, the remaining 10% was released constantly in the following 48 hours (FIG. 14). The release in potassium iodide solution was even faster and 90% of the iodine content was released in 1 hour. The increase in iodine release in potassium iodide solution was due to the higher solubility of iodine in potassium iodide solution (FIG. 15).

EXAMPLE 7

Having demonstrated that the catheters can be effectively coated with a polymer that is programmed to release iodine for periods that are long enough and at concentrations that are high enough to theoretically inactivate the HIV virus, the next experiment consists of effectively proving that the programmable-iodine releasing polymer is able to inactivate the virus. The programmable iodine-loaded polymer was tested using culture plates that are usually used in viral cultures.

Polyurethane-iodine matrix: 24 well plates (Costar) were coated with polyurethane-iodine by spreading 50 microliters of polyurethane-iodine (PU-iodine) solution in tetrahydrofuran (THF, 2.5 weight %) in each well. After solvent evaporation a dark coating was obtained. The iodine concentration in the polyurethane coating was 10, 20, and 30% based on the polyurethane. The total iodine content in the PU-iodine matrices was 120, 240 and 360 micrograms of iodine per well for the 10, 20 and 30 weight % PU-iodine coating. For each concentration, four wells were used.

Figure 16:
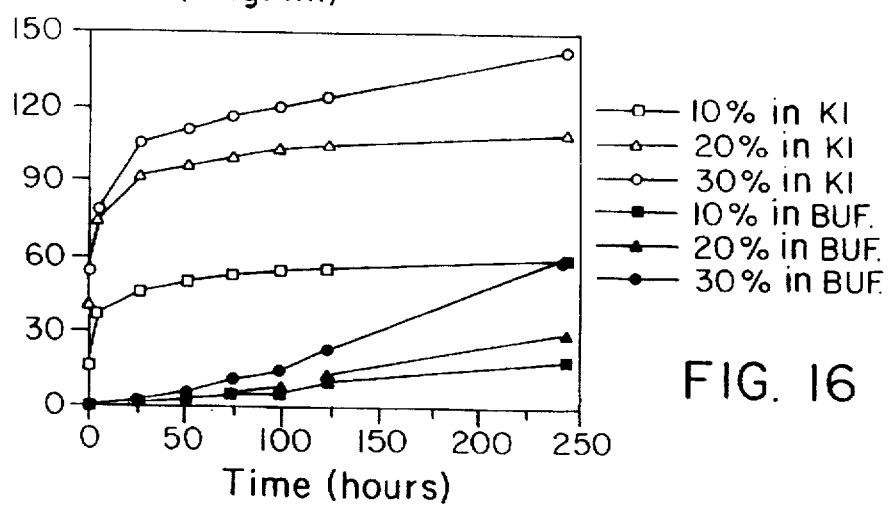
FIG. 16 is a graph of the rate of iodine release from a polymer iodine matrix in potassium iodide.
Figure 17:
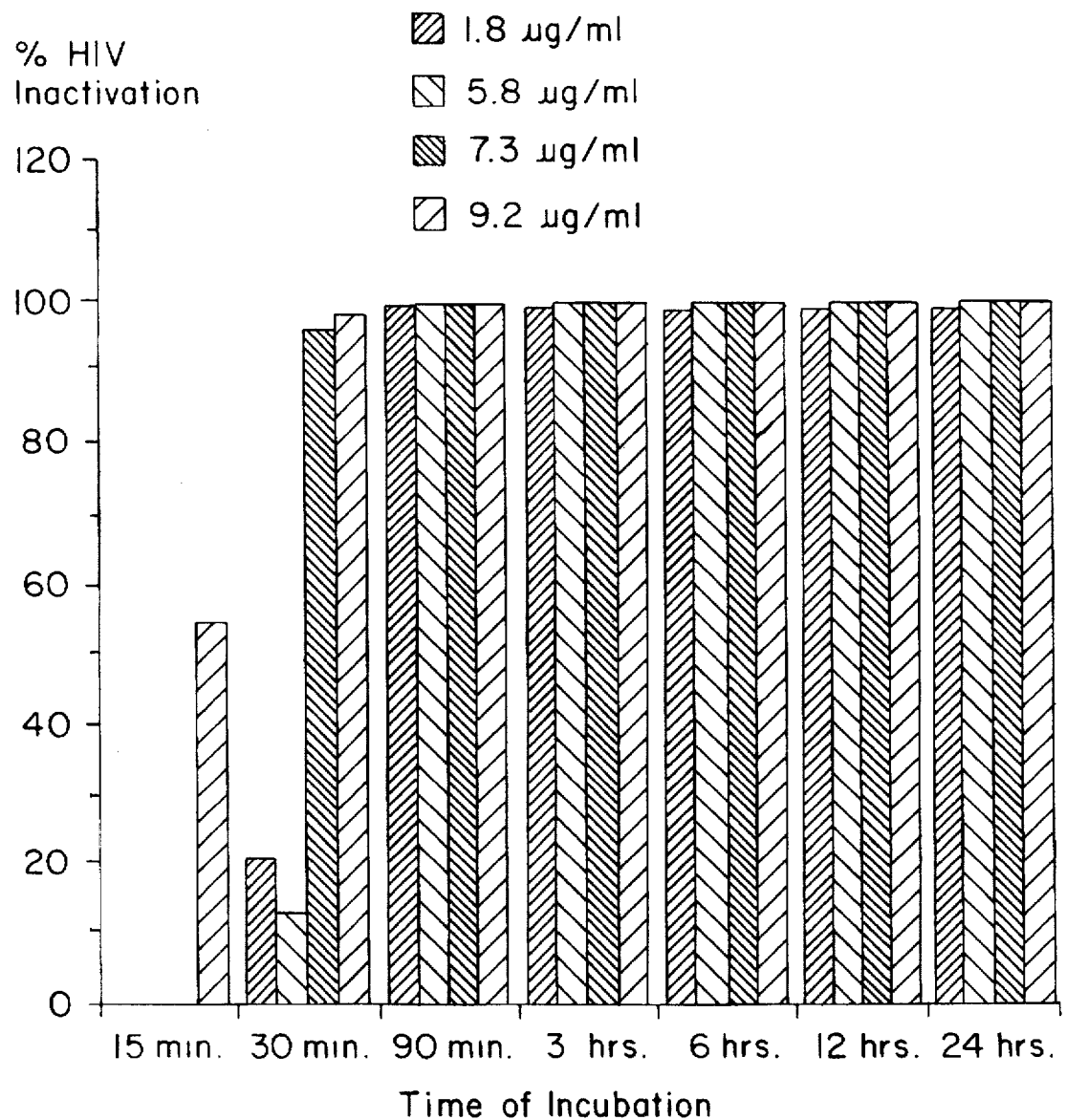
FIG. 17 is a bar chart of the inactivation of HIV virus by the coating of the present invention.

The release of iodine from the polyurethane-iodine matrix in phosphate buffer was very slow and was dependent on the solution in which the polymer is placed. In phosphate buffer solution, a negligible amount of iodine was released in 3 days. On the other hand, in potassium iodide solution, a significant amount of iodine was released for 10 days. About 70 to 80% of the iodine was released in 24 hours, and the rest was released constantly over a period of more than 10 days (FIG. 16).

By changing the thickness of the polymer coating and by using more than one polymer coating (e.g. using a combination of polyurethane-iodine matrix or polyurethane-iodine complexes, with a second coating of polyurethane-iodine complex or uniodized polymer), the amount and duration of iodine release can be programmed at the time of the coating. Using this approach, the duration of iodine release can be sustained for up to several months.

The effectiveness of the polyurethane-iodine coating has been demonstrated with HIV virus grown in tissue culture plates that have been coated with the complex coating of the present invention.

The in-vitro anti-HIV activity of the polyurethane-iodine coated plates was assessed by incubating HIV-3B virus in coated plates for 15 minutes, 30 minutes, 90 minutes, 3 hours, 6 hours, 12 hours and 24 hours prior to infection of the human lymphocyte (MT4) cells (5×100,000 cells/ml) at a multiplicity of infection of 100 ×tissue culture infections dose (TCID) 50. The plates were coated with polymers that release different concentrations of iodine; 1.8, 5.8, 7.3, and 9.2 µg of iodine/ml/hr. for at least the first few hours. The virus, and thus the coated plates, were diluted 1:20 before adding the cells. The infection was allowed to incubate at 37° C. for one hour, at which time the cells were diluted with culture medium RPMI 1640 supplemented with 10% heat-inactivated fetal bovine serum and 10% interleukin-2 to a cell density of 8×10,000 cells/ml. The cells were then seeded onto 96-well plates and incubated at 37° C. Five days later, the cell-free supernatant was analyzed for reverse transcriptase and cells infected with virus exposed to plates coated with the present invention for 24 hours were analyzed for cell growth.

The MT4 cells that were exposed to the polyurethane-iodine complex multiplied as rapidly as control non-infected cells, indicating complete inactivation of the HIV.

A quantitative analysis of the HIV inactivation was done in the polyurethane-iodine complex plates, by analyzing the cell-free supernatant for reverse transcriptase (RT). The data are tabulated in Table I below and summarized in FIG. 17.

Table I indicates that while only partial inactivation of HIV 3B was achieved after 15 minutes incubation in plate number 4, full inactivation of the virus was observed after only 30 minutes incubation in both plates 3 and 4. Complete inactivation of the virus was achieved in all plates after 90 minutes incubation and continued through 24 hours incubation. Interestingly, the cells exposed to virus incubated in the plates for 24 hours grew as rapidly as uninfected cells, indicating that the iodine released in the media did not affect the growth of the MT4 cells themselves.

TABLE I

Analysis of HIV Inactivation by Reverse Transcriptase (RT) assay

| 15 minute incubation Plate * | cpm (average of 3 wells) | % Inhibition of HIV |
|---|---|---|
| Control | 215350 | — |
| 1.8 µg Iodine/ml | 225358 | 0 |
| 5.8 µg Iodine/ml | 234782 | 0 |
| 7.3 µg Iodine/ml | — | — |
| 9.2 µg Iodine/ml | 96907 | 55 |

| Plate | cpm (average of 3 wells) | % Inhibition of HIV |
|---|---|---|
| 30 minute incubation | | |
| Control | 229862 | — |
| 1.8 µg Iodine/ml | 183397 | 21 |
| 5.8 µg Iodine/ml | 201128 | 13 |
| 7.3 µg Iodine/ml | 13219 | 96 |
| 9.2 µg Iodine/ml | 4931 | 98 |
| 90 minute incubation | | |
| Control | 285898 | — |
| 1.8 µg Iodine/ml | 1489 | 99.5 |
| 5.8 µg Iodine/ml | 950 | 99.7 |
| 7.3 µg Iodine/ml | 648 | 99.8 |
| 9.2 µg Iodine/ml | 923 | 99.7 |
| 3 hour incubation | | |
| Control | 259064 | — |
| 1.8 µg Iodine/ml | 948 | 99.7 |
| 5.8 µg Iodine/ml | 739 | 99.7 |
| 7.3 µg Iodine/ml | 512 | 99.8 |
| 9.2 µg Iodine/ml | 622 | 99.8 |
| 6 hour incubation | | |
| Control | 147961 | — |
| 1.8 µg Iodine/ml | 1731 | 99 |
| 5.8 µg Iodine/ml | 917 | 99.4 |
| 7.3 µg Iodine/ml | 621 | 99.6 |
| 9.2 µg Iodine/ml | 460 | 99.7 |
| 12 hour incubation | | |
| Control | 147961 | — |
| 1.8 µg Iodine/ml | 1731 | 99 |
| 5.8 µg Iodine/ml | 917 | 99.4 |
| 7.3 µg Iodine/ml | 621 | 99.6 |
| 9.2 µg Iodine/ml | 460 | 99.7 |
| 24 hour incubation | | |
| Control | 131116 | — |
| 1.8 µg Iodine/ml | 1970 | 98.5 |
| 5.8 µg Iodine/ml | 859 | 99.4 |
| 7.3 µg Iodine/ml | 636 | 99.5 |
| 9.2 µg Iodine/ml | 552 | 99.6 |

| Mock-Infected Plate | cpm | |
|---|---|---|
| Control | 559 | |
| 1.8 µg Iodine/ml | 565 | |
| 5.8 µg Iodine/ml | 503 | |
| 7.3 µg Iodine/ml | 531 | |
| 9.2 µg Iodine/ml | 501 | |

* concentrations are prior to dilution

The anti-HIV effectiveness of the coating of the present invention is further shown by the following: Commercially available central venous catheters (obtained from Baxter Pharmaceuticals), were coated with polyurethane-iodine complexes. Coated and control uncoated catheters were divided into 0.9 cm pieces, the surface of each piece being equivalent to the surface of each of the wells in the culture plates. The catheter pieces were exposed to UV radiation to sterilize the pieces. The pieces of catheter were then coated with a complexed polymer containing 9.2 μg iodine/ml. For inactivation of HIV, it is preferred that the catheter be coated on both the inside and outside surfaces. Since the catheter tube is coated both on the inside and on the outside, this would correspond to an area of about 1.77 cm². Several experiments were performed, each involving MT4 cells, using the HIV-1, strain 3B, as the virus inoculum.

Experiment 1: Catheter pieces were immersed in virus solution for 15, 30, 90, and 120 minutes and then the catheter pieces were used to inoculate MT4 cells. The cells were allowed to grow for 5 days at which time the cell-free supernatant was assayed for the presence of reverse transcriptase (RT). Table II presents the data obtained.

TABLE II

Measurement of Virus Remaining on
Catheter Pieces after Incubation with HIV 3B

| Incubation Time minutes | Control Catheter RT cpm | Coated Catheter RT cpm |
|---|---|---|
| 15 | 6290 | 130 |
| 30 | 2576 | 108 |
| 90 | 1342 | 185 |
| 120 | 1080 | 242 |

The results indicated 97.93% inhibition of viral replication within 15 minutes in the coated group, as compared to the control, and this inhibition was sustained over 2 hours.

Experiment 2: MT4 cells were infected with HIV 3B for one hour, at which time the infected cells were exposed to catheter pieces. Five days later, the cell-free supernatant was assayed for the presence of RT as shown in Table III.

TABLE III

Ability of MT4 Cells to Support Viral
Replication in the Presence of Catheter Pieces

| | Control Catheter | Coated Catheter |
|---|---|---|
| RT (cpm) | 24991 | 455 |

The results indicated 98.17% inhibition of viral replication in the coated group, as compared to the control.

Experiment 3: Catheter pieces were immersed in HIV 3B for 10 minutes. The catheter pieces were removed and kept at 100% humidity for 15 minutes, 30 minutes, 2 hours and 4 hours; at which time the catheter pieces were used to inoculate MT4 cells. Five days later, the cell-free supernatant was assayed for the presence of RT and the results are given in Table IV.

TABLE IV

Ability of Catheter Pieces to Retain
Viable HIV 3B After Removal From Virus Solution

| Incubation Time minutes | Control Catheter RT cpm | Coated Catheter RT cpm |
|---|---|---|
| 15 | 184854 | 149 |
| 30 | 195101 | 108 |

TABLE IV-continued

Ability of Catheter Pieces to Retain
Viable HIV 3B After Removal From Virus Solution

| Incubation Time minutes | Control Catheter RT cpm | Coated Catheter RT cpm |
|---|---|---|
| 120 | 176870 | 296 |
| 240 | 5997 | 103 |

The results indicated 99.91% inhibition of viral replication within 15 minutes in the coated group, as compared to control, and this inhibition was sustained over 4 hours.

Experiment 4: Catheter pieces were immersed in HIV 3B for 2 hours. At this time, the catheter pieces were removed and the virus was used in inoculate MT4 cells. Five days later, the cell-free supernatant was assayed for the presence of RT. The data is shown in Table V.

TABLE V

Ability of Catheter Pieces to Inactivate
HIV 3B During 2 Hour Exposure Time

| | Control Catheter | Coated Catheter |
|---|---|---|
| RT (cpm) | 45125 | 410 |

The results indicated 99.09% inhibition of viral replication in the coated group, as compared to the control.

Thus, it is evident that the amount of iodine released from the coated catheters is significant and is sufficient to inactivate the HIV virus.

EXAMPLE 8

To demonstrate the effectiveness of the polymer-iodine coating on bacteria, the common and highly pathogenic human bacteria, Staphylococcus Aureus, was studied in-vitro and in-vivo (rats). The tip of a tracheal tube device was coated as follows: 0.5 grams of iodine crystals were dissolved in tetrahydrofuran solution containing 1.5 grams of segmented polyurethane PU (Estane). The tip of a tracheal tube, size 5.5 mm (Portex Inc., Wilmington, Mass.) was coated by dipping the tip in the iodine/polymer solution (total area 3 cm²). After solvent evaporation, the dark uniform matrix coating of about 0.2 mm was coated with Ethylene Vinyl Acetate, (EVAc) coating by dipping in a chloroform solution of EVAc. The EVAc coating of 0.05 mm is to prevent iodine release from the surface by sublimation. Alternatively, the tube is first coated with polyurethane and then loaded with iodine by immersing the coated tube in a 20% $I_2$/KI solution in water. The impregnated PU/iodine complex coating was then dried in room air and coated with EVAc. in vitro iodine release was determined in 0.1M KI solution at 37° C. the iodine released in the solution was determined by UV absorption at 310 nm.

The in vivo and biological activity of iodine released from the tube coating was then studied. Portions of an iodine-coated PVC tracheal tube were cut and subcutaneously implanted in 6 rats. The first 3 animals were sacrificed at day 7 and the devices were removed and placed for 3 consecutive days on an agar plate for antibacterial activity test as described below. At day 10, the tubes were placed in 20 ml 0.1M KI solution for in vitro release study. The antimicrobial activity was determined again at day 16. The second group of 3 rats were sacrificed at day 14 and the antimicrobial and the in vitro release was determined. The antimicrobial activity was determined using agar plates (Bactopepton 1%, yeast extract 0.5%) seeded with pathogenic Staphylococcus Aureus that was cultured from a patient's implanted catheter. The tubes were placed on the agar plate and incubated for 24 hours and the inhibition zone measured. The agar plates were replaced with fresh plates daily. The results are summarized in Table VI. As seen, the drug release is decreasing exponentially with time, but significant amounts of iodine are still released from the devices even after 23 days in vitro. All devices were active against bacteria for 21 days. The iodine release from the implantable devices after removal was lower when tested in vitro, which indicates that iodine is released faster in vivo. Histology of the site of implantation showed no irritation or tissue necrosis caused by the devices.

TABLE VI in vitro, in vivo iodine release, and antibacterial activity of iodine-coated tubes:

| Time (days) | In vitro ($\mu g/cm^2/hr$) | In vivo (7 days) | In vivo (14 days) | Antibacterial activity (Inhibition zone, in mm) |
|---|---|---|---|---|
| 1 | 108 | I | I | 65* (no growth) |
| 2 | 25 | N | N | 65* (no growth) |
| 3 | 23 | | | 55* |
| 4 | 23 | V | V | 52* |
| 5 | 21 | I | I | 45* |
| 6 | 19 | V | V | 12# |
| 7 | 18 | O | O | 12# |
| 8 | 16 | 35* | | 10# |
| 9 | 16 | 30* | | |
| 10 | 12 | 7# | | 8# |
| 11 | 10 | 7# | | 8# |
| 12 | 9 | 6# | | 7# |
| 13 | 8 | 6# | | |
| 14 | 7 | 30* | 27* | 32* |
| 16 | 5 | 5.6# | 28* | 4.2# |
| 17 | 5 | 4.7# | 27* | 3.5# |
| 19 | 4 | 3.3# | 2.6# | 2.3# |
| 21 | 4 | 3.1# | 1.4# | 2.0# |
| 23 | 4 | 3# | inactive* | inactive* |

*Diameter of inhibition zone, mm
in vitro iodine release, ($\mu g/cm^2/hr$)

EXAMPLE 9

The stability of the polymer/iodine coating was demonstrated. Endotracheal tubes made of polyvinylchloride (Portex) were matrix coated with polyurethane-iodine and further coated with a rate-controlling second layer of plain polymer. Other endotracheal tubes were coated with a single polyurethane-iodine complex coat without a second layer. The coated tubes were each packed in a polyethylene sealed bag and stored at 4° C. and 25° C. The percent iodine remaining in each coated device was evaluated after one month of storage, by dissolving the iodine coating with tetrahydrouran (THF) and determining the iodine content by UV detection at 310 nm as compared to an iodine free endotracheal tube. The devices stored at 4° C. retained 98% and 92% of the original iodine respectively. The devices stored at 25° C. retained 95% and 75% of their iodine content after one month, respectively. After 12 months of storage at 25° C., the iodine content of the matrix coating retained more than 90% of the original iodine content, while the single polyurethane-iodine complex coat lost more than 50% of its original iodine content. This experiment demonstrates the advantage of using a second coating with respect to storage stability.

The polymer-iodine coating is effective when used with hepatitis B virus (HBV), other viruses, bacteria, fungi, mycobacteria and spores. Iodine is a universal antiinfective agent with no known microbial resistance. The coated catheter of the present invention protects the patient from infectious viruses and bacteria which may enter the patient while the catheter is inserted into either an incision in the skin of the patient or into a body cavity. The coated catheter of the present invention also protects health care providers from becoming infected from infectious viruses and bacteria which may be present on catheters which the health care provider contacts during or after removal of a catheter from the patient. A small abrasion, laceration or opening in the skin of the health care provider could be enough to allow the health care provider to be infected. The coated catheter of the present invention inhibits the viruses and bacteria to significantly reduce the probability of the health care provider becoming infected. Although catheters have been specifically identified, the coatings (complex, matrix and multiple) of the present invention may also be used on other instruments, equipment and supplies in the health services environment to inhibit infectious viruses, bacteria and germs.

The present invention will be further understood by reference to the following non-limiting examples.

EXAMPLE 10

Release of Nystatin from a coated tracheal tube

The tip of a tracheal tube device was coated as follows: 18% w/w nystatin (1 mg, 5,000 Units) in an ethylenevinyl acetate (EVA) coating was prepared by dipping the tip (up to the balloon, total area of coating 15 cm$^2$) of a tracheal tube, size 8.5 mm, style XL (Portex Inc., Wilmington, Mass.) in a 10 weight % EVA solution containing 18 weight % nystatin in dichloromethane. Solvent was evaporated to yield a 0.24% mm thick coating. The coating was overlaid with a thin layer (0.05 mm) of drug free EVA to slow the drug release.

Figure 18:
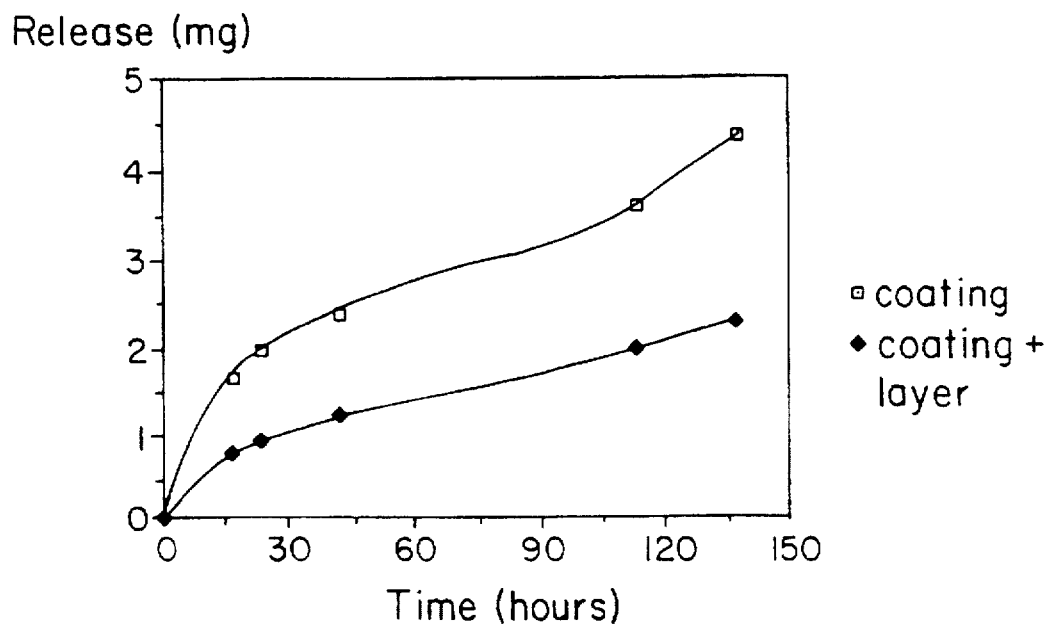
FIG. 18 is a graph of the release of nystatin (mg) over time (hours) from a tracheal tube coated with ethylene vinyl acetate (EVA) containing 18 weight % nystatin (squares) and the same tube overlaid with non-drug loaded EVA (dark diamonds).

Nystatin release from the tube was determined in 0.1M phosphate buffer pH 7.4 at 37° C., by measuring ultraviolet (UV) absorbance at 250 nm. The release of nystatin from coated and uncoated devices is shown in FIG. 18. As seen, 4.5 mg of drug is released from the coated tube. The release rate is decreased by further coating of the tube with a plain layer of EVA. The release can be increased or decreased by changing the drug loading or using different polymeric material for coating.

EXAMPLE 11

In Vitro Release of Antimicrobial Iodine from a Polymer Coated Tracheal Tube

Iodine is a widely used broad spectrum antimicrobial agent. It is used in solutions, soaps, creams, paste, etc. A tracheal tube was coated with an iodine releasing system, as follows: 0.5 grams of iodine crystals were dissolved in tetrahydrofuran solution containing 1.5 grams of segmented polyurethane, PU (Estain™, Goodrich, Ill.). The tip of a tracheal tube, size 5.5 mm (Portex Inc., Wilmington, Mass.) was coated by dipping the tip in the iodine/polymer solution (total area of coating 3 cm$^2$). After solvent evaporation, the resulting dark uniform coating of about 0.2 mm was coated with an EVA coating by dipping in a chloroform solution of EVA. The EVA coating of 0.05 mm is to prevent iodine release from the surface by sublimation.

Figure 19:
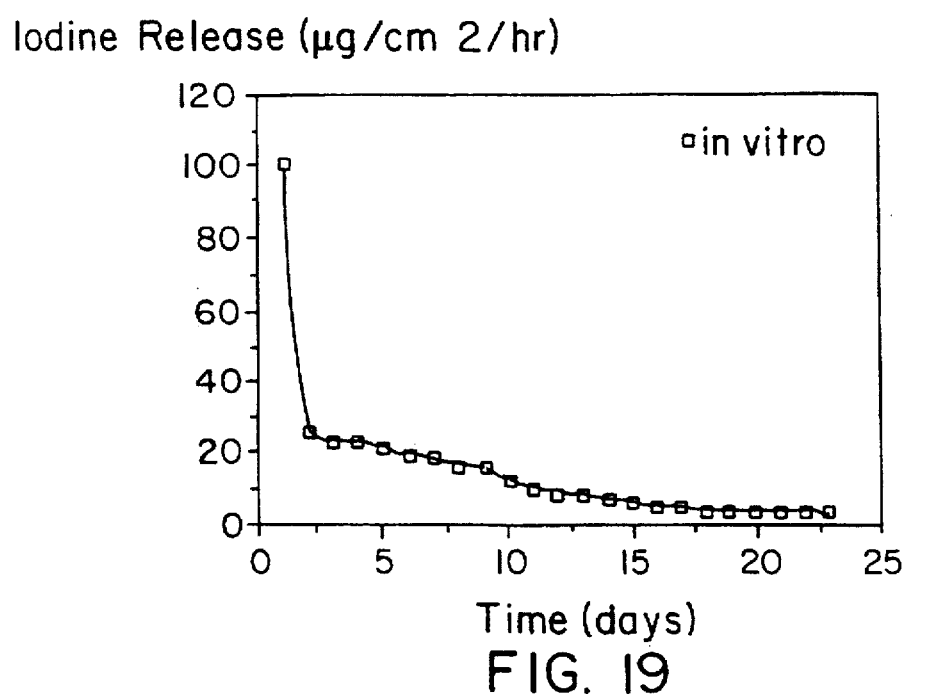
FIG. 19 is a graph of iodine release ($\mu g/cm^2/hr$) from a catheter having a polyurethane coating containing iodine, overlaid with non-drug loaded EVA, over time (days).
Figure 20:
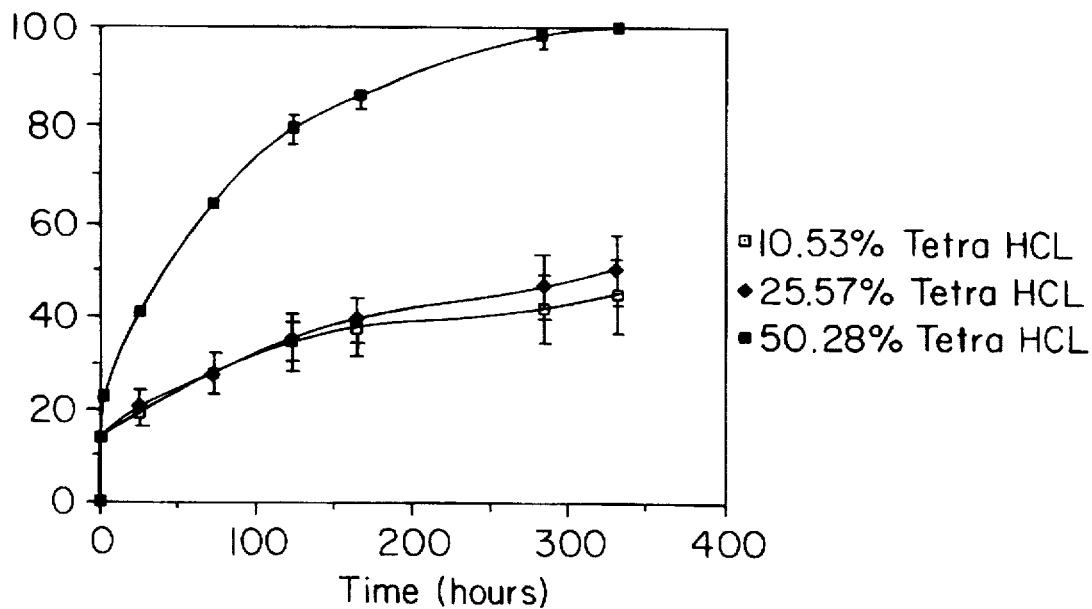
FIG. 20 is a graph of percent of tetracycline release from silicon coatings over time (hours) for 10.53% tetracycline-HCl (squares); 25.57% tetracycline-HCl (dark diamonds); and 50.28% tetracycline-HCl (dark squares).
Figure 21:
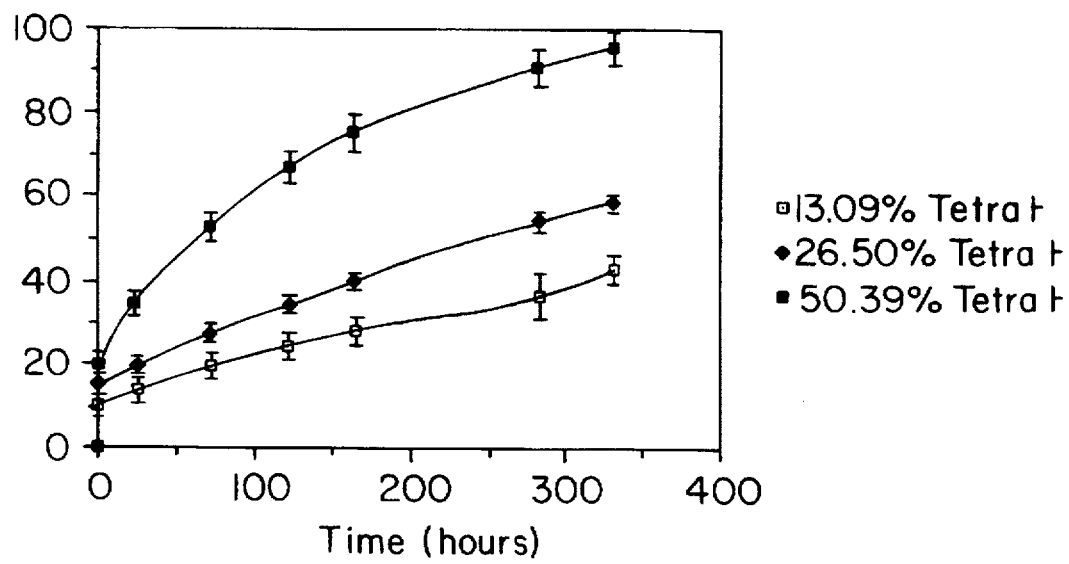
FIG. 21 is a graph of percent of tetracycline release from EVA coatings over time (hours) for 13.09% tetracycline-HCl (squares); 26.50% tetracycline-HCl (dark diamonds); and 50.39% tetracycline-HCl (dark squares).
Figure 22:
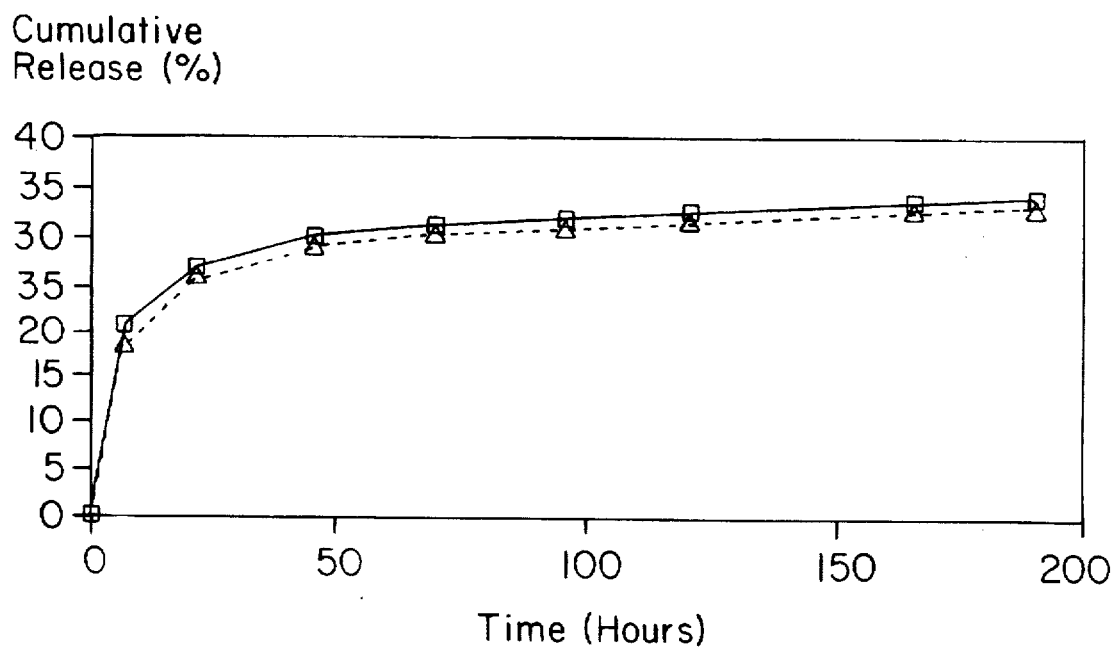
FIG. 22 is a graph of the cumulative percent release of dexamethasone from polyurethane coated tracheal tube over time (hours) for 5% dexamethasone (square) and 10% dexamethasone (triangle).
Figure 23:
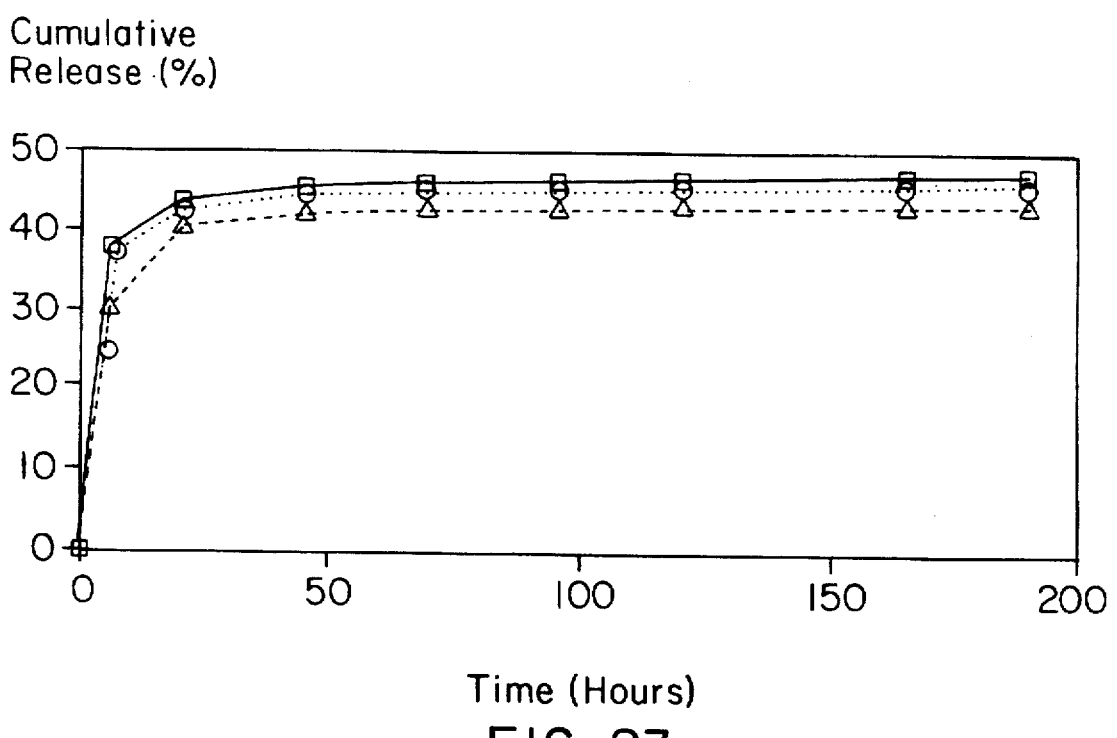
FIG. 23 is a graph of the cumulative percent release of dexamethasone from EVA coated tracheal tube over time (hours) for 5% dexamethasone (squares); 10% dexamethasone (triangle); and 20% dexamethasone (circles).

Alternatively, the tube was first coated with plain (non-drug loaded) polyurethane and then loaded with iodine by immersing the coated tube in a 20% I$_2$/KI solution in water. The impregnated PU/iodine coating was then dried in room air and coated with plain EVA. In vitro iodine release was determined in a 0.1N KI solution at 37° C. by measuring UV absorption at 310 nm. The release of iodine from the tube is shown in FIG. 19.

EXAMPLE 12
In Vivo and Biological Activity of Iodine Released from Tube Coating Devices of iodine coated tubes, cut from a PVC tracheal tube, as prepared in Example 11, were subcutaneously implanted in six rats (two groups of three rats). The first group of three animals were sacrificed at day 7 and the devices were removed and placed for three consecutive on an agar plate for antibacterial activity test as described below. At day 10 the tubes were placed in 20 ml 0.1N KI solution to measure release in vitro. The antimicrobial activity was determined again at day 16. The second group of 3 rats were sacrificed at day 14 and the antimicrobial activity and the in vitro release from the devices were determined. The antimicrobial activity was determined using agar plates (Bactopepton 1%, yeast extract 0.5%) seeded with pathogenic Staphylococcus aureus (removed from a catheter implanted in a patient). The tubes were placed on the agar plate and incubated for 24 hours and the inhibition zone was measured. The agar plates were replaced with fresh plates daily. As seen, the drug release decreases exponentially with time, but significant amounts of iodine are still being released from the devices even after 23 days in vitro. All devices were active against bacteria for 21 days. The drug release from the implanted devices after removal from the animals was lower, as compared with the in vitro data, which indicates that iodine is released faster in vivo. Histology of the site of implantation showed that no irritation or necrosis was caused by the devices

EXAMPLE 13
Tetracycline-HCl Release From Silicon and EVA Films

Tetracycline-HCl was incorporated into a silicone polymer for subsequent release. Silicon polymers are used to prepare various sizes and shapes of silicone tubings and implantable devices, as well as portions thereof.

In the experiment, silicone devices were prepared using Medical Grade elastomer (Dow Corning) and a curing agent (Dow Corning) mixed at a ratio of 10:1. To the mixture was added 10.25 w/w tetracycline-HCl mixed well to form a yellow uniform mass. The mixture was cast into a 1 mm film and cured for 24 hours at room temperature. The film was cut into 5×5 mm slabs which weighed 50 mg each.

Ethylene Vinyl Acetate (EVA) devices were prepared by mixing 10 and 25% tetracycline-HCl in the polymer and casting to form a 1 mm film. The film was cut into 5×5 mm slabs which weighed 50 mg each.

The release of the drug from these devices (12 mg each) was studied in phosphate buffer pH 7.4 at 37° C. for 332 hours. Tetracycline was determined by measuring UV absorbance at 275 nm. The results are summarized in FIGS. 20 and 21.

EXAMPLE 14
Release of Dexamethasone from Coated Blue Line Tracheal Tubing

The release of Dexamethasone LOT #726DK) from polyurethane (Estane™ BF Goodrich) and EVA (Aldrich) coated tubing was studied. A solution of 5% (w/v) Estane™ in THF along with a 5% solution of EVA in methylene chloride were first prepared. Dexamethasone was then incorporated into the solution, at ratios of 5 and 10% (w/w) Dexamethasone to Estane™ and 5, 10 and 20% (w/w) Dexamethasone to EVA. The solutions were then vortexed for 5 minutes. The amount of polymer coating and dexamethasone in the device is summarized in Table 2.

The tubing (4.115 cm²) was dipped one time into the one of the solutions. Release from ten samples for 190 hours was measured. The release of drug from the coatings is described in FIGS. 22 and 23. The release from both coatings is characterized by an initial release followed by a continuous release of small amounts of drug.

TABLE 2

Relative amounts of Dexamethasone in Estane ™ and EVA coatings.

| Coating | Coating + Dexamethasone mg | Dexamethasone mg |
|---|---|---|
| 5% DEXAMETHASONE IN EVA | 5.8 | .29 |
| 10% DEXAMETHASONE IN EVA | 5.1 | .51 |
| 20% DEXAMETHASONE IN EVA | 4.0 | .80 |
| 5% DEXAMETHASONE IN ESTANE ™ | 9.6 | .48 |
| 10% DEXAMETHASONE IN ESTANE ™ | 10.7 | 1.07 |

EXAMPLE 15
Release of Triamcinolone from Estane™ Coated Blue Line Tracheal Tubing A 5% (w/v) solution of Estane™ in THF was prepared and allowed to stand for 4 hours. Triamcinolone (lot #493rx) was then added to the solution at ratios of 4, 10 and 20% (w/w) Triamcinolone to Estane™. The amount of polymer coating and triamcinolone in the device is summarized in Table 3. These solutions were then vortexed for 5 minutes. The tubing (4.115 cm²) was then dipped into the solution one time, and left to cure for 24 hours. Duplicates of the samples were prepared for a total of six samples.

Figure 24:
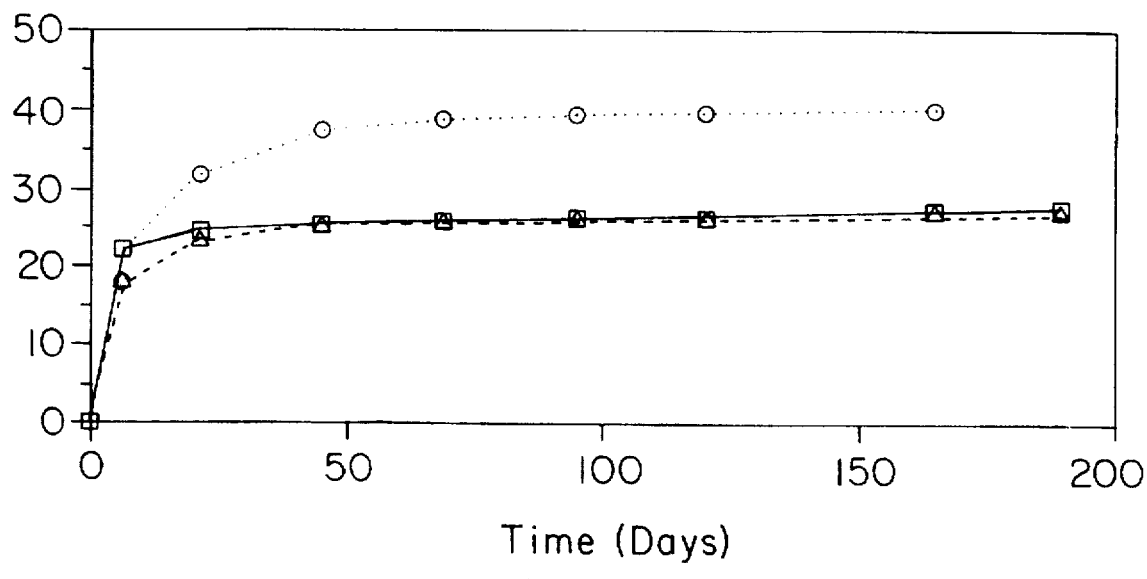
FIG. 24 is a graph of the cumulative percent release of triamcinolone from polyurethane coated tracheal tube over time (days) for 5% triamcinolone (squares); 10% triamcinolone (triangles); and 20% triacinolone (circles).

The release was followed for several weeks. The data in FIG. 24 shows the release up to 190 hours. As is evident, the release from both coatings is characterized by an initial burst of release followed by a continuous release of small amounts of drug.

TABLE 3

Relative Amounts of Triamcinolone in Estane ™ Coatings

| Coating | Coating + Triamcinolone mg | Triamcinolone mg |
|---|---|---|
| 5% TRIAMCINOLONE | 9.1 | .46 |
| 10% TRIAMCINOLONE | 11.8 | 1.18 |
| 20% TRIAMCINOLONE | 6.8 | 1.36 |

EXAMPLE 16
Release of Dexamethasone from Silastic Coated Silicone Procedure

Implant Grade Dispersion Silastic (lot #hh90910), 13% Silastic in methyl chloroform, was diluted to 5% using methylene chloride. The solution was left to stand for 4 hours until the solution was homogeneous. To 20 ml of the solution, 5, 10 and 20% (w/w) Dexamethasone (lot #726dk) to Silastic was added. The solution was then vortexed for 5 minutes to ensure a good mixture. The amount of polymer coating and triamcinolone in the device is summarized in Table 4.

TABLE 4

Relative Amounts of Dexamethasone in Silastic Coated Silicon Tubing

| Coating | Coating + Dexamethasone mg | Dexamethasone mg |
|---|---|---|
| 5% DEXAMETHASONE | 4.4 | .22 |
| 10% DEXAMETHASONE | 3.5 | .35 |
| 20% DEXAMETHASONE | 2.6 | .52 |
| 20% DEXAMETHASONE (3 DIPPINGS) | 8.9 | 1.78 |
| 20% DEXAMETHASONE (ear ventilation tube) | 1.0 | .20 |

Figure 25:
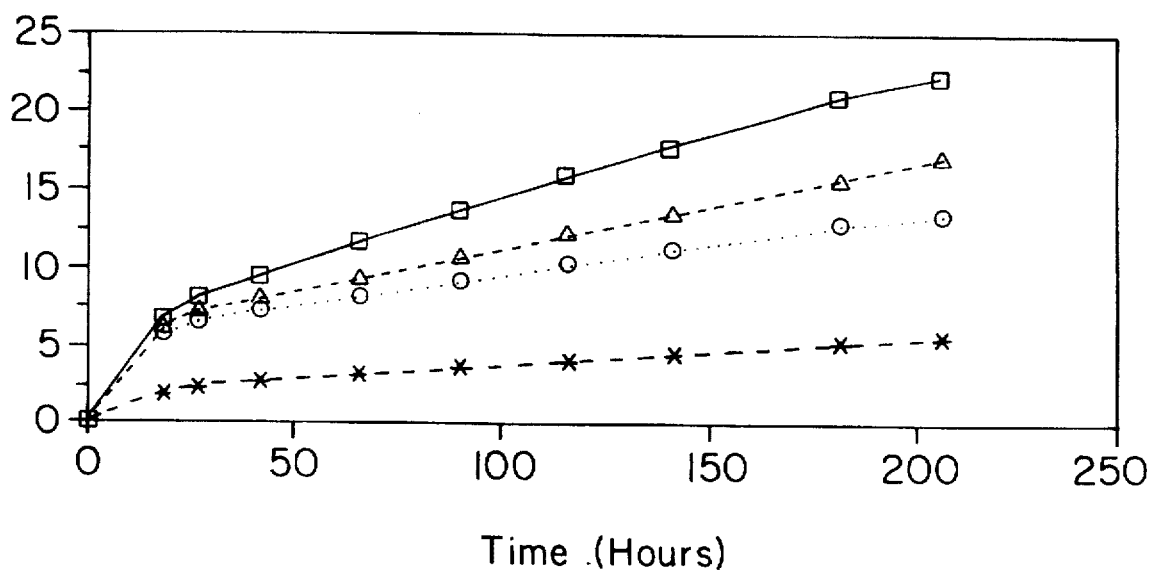
FIG. 25 is a graph of the cumulative percent release of dexamethasone from silastic coated silicone, part of a tracheal device, over time (hours) for 5% dexamethasone (squares); 10% dexamethasone (triangles); 20% dexamethasone (circles); and 20% dexamethasone, three dippings (-*-).
Figure 26:
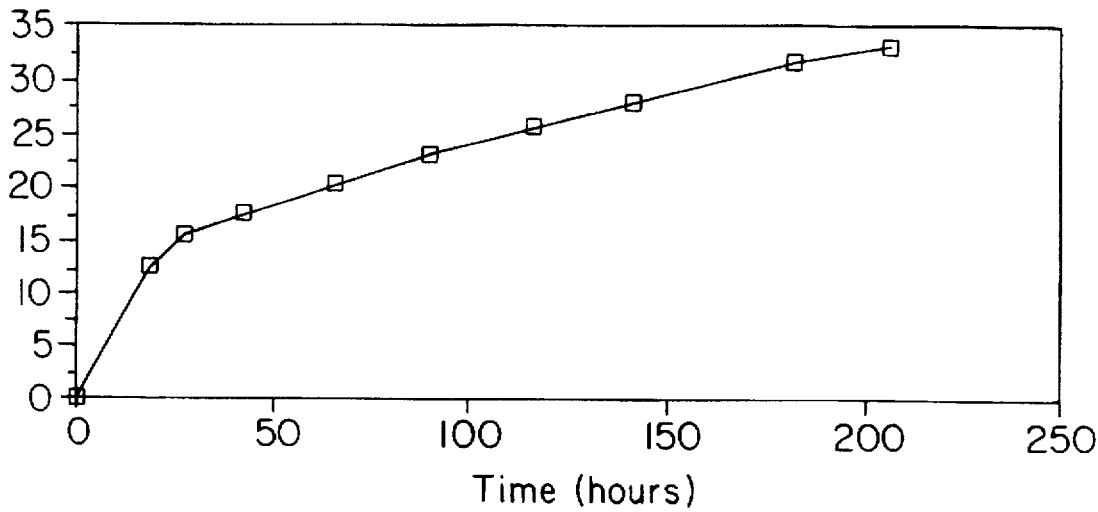
FIG. 26 is a graph of the cumulative percent release of dexamethasone from silastic coated ear ventilation tube (200 µg drug) over time (hours) for 20% dexamethasone (squares).

Two samples of silicone tubing were dipped one time in each of the three solutions. A silicone tube was also dipped three times in the 20% solution, as well as a Xomed Products-ear ventilation device. The release data over 206.5 hours is shown in FIGS. 25 and 26. As is apparent, the release from both coatings is characterized by an initial burst of release followed by a steady release of the drug for a long period of time.

EXAMPLE 17

Release of Triamcinolone from Estane™ Coated Teflon™ Tubing

Procedure

A solution of 5% (w/v) Estane™ in THF was prepared by dissolving 1 g of Estane™ in 20 ml of THF. This solution was allowed to stand for four hours, or until homogeneous. 10 and 20% (w/w) Triamcinolone to Estane™ was added and the solution was vortexed until uniform. Teflon™ tubing of approximately 2.54 cm in length and 6 mm in diameter was coated by dipping once in the Estane™ solution and leaving to dry in the room air. A thin coating of about 0.2 mm which adheres very well to the tubing was produced. One sample of each coating was used in the study, each drying evenly on the surface of the Teflon™. The coating remained intact during the in vitro studies.

Figure 27:
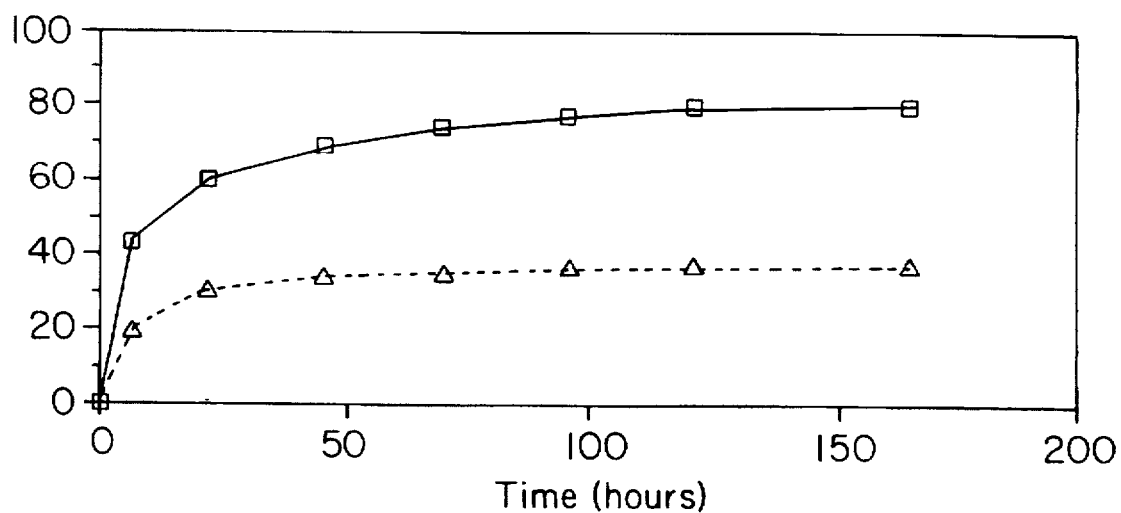
FIG. 27 is a graph of the cumulative release of triamcinolone from polyurethane coated Teflon™ tubing over time (hours) for 10% triamcinolone (squares) and 20% triamcinolone (triangles).

The data showing release through 165 hours is represented in FIG. 27. The amount of polymer coating and triamcinolone in the device is summarized in Table 5. As seen, the release from both coatings is characterized by an initial release followed by a steady release of the drug for a long period of time.

TABLE 5

Relative Amounts of Triamcinolone in Estane ™.

| Coating | Coating + Triamcinolone mg | Triamincinolone mg |
|---|---|---|
| 10% TRIAMCINOLONE | 3.8 | .38 |
| 20% TRIAMCINOLONE | 3.2 | .64 |

Modifications and variations of the compositions, and methods for making and using thereof, of the present invention will be obvious to those skilled in the art and are intended to come within the scope of the appended claims.

The present invention also provides a device and method whereby a tube or catheter and other medical device, has thereon a surface compatible polymer coating having iodine complexed and/or matrixed therein, so as to provide for the immediate and/or sustained release of the iodine therefrom for inhibiting dissemination of germs during use thereof. The present invention provides polymer coated devices in which the iodine release is localized and programmable, as desired.

Obviously, many modifications may be made without departing from the basic spirit of the present invention. Accordingly, it will be appreciated by those skilled in the art that within the scope of the appended claims, the invention may be practiced other than has been specifically described herein.

We claim:

1. An endotracheal or tracheostomy tube for implantation into the body and coming into contact with body tissue and fluids comprising said endotracheal or tracheostomy tube having thereon a biocompatible, nonbioerodible polymer dissolved in a solvent to form a solution, the solution being disposed on the exterior surface of the device and the solvent removed to form a uniform coating on the endotracheal or tracheostomy tube thereby coating said exterior surface and wherein said polymer coating is formed of non-hydrogel polymer being insoluble in a biological medium and soluble in an organic solvent, with said polymer coating containing effective amounts of iodine and an anti-inflammatory agent sorbed therein, such that the iodine is released over a period of at least twenty-four hours by diffusion while the endotracheal or tracheostomy tube is implanted into the body.

* * * * *